(12) United States Patent
Fujii et al.

(10) Patent No.: US 9,221,949 B2
(45) Date of Patent: Dec. 29, 2015

(54) RESIN, OPTICAL MATERIAL, AND OPTICAL DEVICE

(75) Inventors: Shunsuke Fujii, Ichihara (JP); Shintaro Maekawa, Ichihara (JP); Hitoshi Onishi, Chiba (JP); Akifumi Kagayama, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 152 days.

(21) Appl. No.: 14/003,719

(22) PCT Filed: Mar. 9, 2012

(86) PCT No.: PCT/JP2012/001654
§ 371 (c)(1),
(2), (4) Date: Sep. 6, 2013

(87) PCT Pub. No.: WO2012/120901
PCT Pub. Date: Sep. 13, 2012

(65) Prior Publication Data
US 2014/0001950 A1  Jan. 2, 2014

(30) Foreign Application Priority Data

Mar. 9, 2011 (JP) ................. 2011-051629
Sep. 20, 2011 (JP) ................. 2011-204461

(51) Int. Cl.
| | |
|---|---|
| *C08G 69/42* | (2006.01) |
| *G02B 1/04* | (2006.01) |
| *F21V 5/00* | (2015.01) |
| *G02B 1/00* | (2006.01) |
| *H05B 33/22* | (2006.01) |
| *C08G 12/06* | (2006.01) |
| *C08G 12/22* | (2006.01) |
| *C08G 69/00* | (2006.01) |
| *C08G 73/02* | (2006.01) |
| *C07C 249/16* | (2006.01) |
| *C08L 79/06* | (2006.01) |
| *C07C 251/86* | (2006.01) |

(52) U.S. Cl.
CPC ............ *C08G 69/42* (2013.01); *C08G 12/06* (2013.01); *C08G 12/22* (2013.01); *C08G 69/00* (2013.01); *C08G 73/028* (2013.01); *F21V 5/00* (2013.01); *G02B 1/00* (2013.01); *G02B 1/04* (2013.01); *H05B 33/22* (2013.01); *C07C 249/16* (2013.01); *C07C 251/86* (2013.01); *C08L 79/06* (2013.01)

(58) Field of Classification Search
CPC ...... C07C 249/16; C07C 251/86; C08L 79/06
USPC .............. 362/311.03; 528/208, 271
See application file for complete search history.

(56) References Cited

U.S. PATENT DOCUMENTS

2003/0064235 A1    4/2003  Okawa et al.

FOREIGN PATENT DOCUMENTS

| JP | 41-016316 B1 | 9/1966 |
|---|---|---|
| JP | 57-088156 A | 6/1982 |
| JP | 04-117354 | 4/1992 |
| JP | 2007-269819 | 10/2007 |
| JP | 2009-057483 A | 3/2009 |
| JP | 2010-070513 A | 4/2010 |
| WO | WO 02/12926 A1 | 2/2002 |
| WO | WO 2006/003905 A1 | 1/2006 |

OTHER PUBLICATIONS

Ono et al ("Optodynamers: expression of color and fluorescence at the interface between two films of different dynamic polymers", Chem. Commun., 2007, 4360-4362), Nov. 2007.*
International Search Report (PCT/ISA/210) mailed on Jun. 12, 2012, by the Japanese Patent Office as the International Searching Authority for International Application No. PCT/JP2012/001654.
W. Skene et al., "Dynamers: Polyacylhydrazone reversible covalent polymers, component exchange, and constitutional diversity", Proc Natl Acad Sci USA, 2004, p. 8270-8275, vol. 101, No. 22.
Kim et al., "Synthesis of Polyhydrazones by Diazo Coupling Reaction of Bisacetoacetamides with Diazonium Salts", Polymer Bulletin, May 1, 2001, vol. 46, No. 4, pp. 285-290. (XP001071335).
Labib et al., "Copper(II) and Nickel(II) Metallopolymers Derived from Polyacylhydrazones", Transition Metal Chemistry, Dec. 1, 2000, vol. 25, pp. 700-705. (XP055127914).
Folmer-Andersen et al., "Constitutional Adaptation of Dynamic Polymers: Hydrophobically Driven Sequence Selection in Dynamic Covalent Polyacylhydrazones", Angewandte Chemie International Edition, Sep. 28, 2009, vol. 48, No. 41, pp. 7664-7667. (XP055127912).
Maeda et al., "Dynamic Covalent Polymers: Reorganizable Polymers with Dynamic Covalent Bonds", Progress in Polymer Science, Jul. 1, 2009, vol. 37, No. 7, pp. 581-604. (XP026099488).
Extended European Search Report dated Jul. 17, 2014, issued by the European Patent Office in the corresponding European Application No. 12755454.1. (7 pages).
Ono, Takashi et al.; "Dynamic Polymer Blends-Component Recombination Between Neat Dynamic Covalent Polymers at Room Temperature", The Royal Society of Chemistry 2005, pp. 1522-1524.
Ono, Takashi et al.; "Soft-To-Hard Transformation of the Mechanical Properties of Dynamic Covalent Polymers through Component Incorporation", The Royal Society of Chemistry 2007, pp. 46-48.
Troy, Robert C. et al.; "POLY(N-N-Diacylhydrazone)s: Polymers Containing Imide and Imine Functions linked by Nitrogen-Nitrogen Bonds", Journal of Polymer Science: Polymer Letters Edition, vol. 22, pp. 113-118, 1984.

* cited by examiner

*Primary Examiner* — Gregory Listvoyb
(74) *Attorney, Agent, or Firm* — Buchanan, Ingersoll & Rooney PC

(57) ABSTRACT

The purpose of the invention is to provide a resin, which has a high refractive index, excellent heat resistance and moldability, and high transparency, and is useful as a material for configuring optical devices, etc. The invention provides a resin comprising acyl hydrazone bonds and having a number average molecular weight of 500-500,000, wherein the acyl hydrazone bond equivalent is 100-4000.

14 Claims, 4 Drawing Sheets

RESIN, OPTICAL MATERIAL, AND OPTICAL DEVICE

TECHNICAL FIELD

The present invention relates to a resin that is suitable as a constituent material for optical devices and the like, and an optical material and an optical device using the resin.

BACKGROUND ART

Resin materials having high refractive indices have high processability as compared with conventional glass materials, and are useful for optical materials that are intended to construct optical devices such as optical lenses, optical fibers and light waveguides. Among them, polycarbonates, polyurethanes, polyesters, polyamides, and the like are widely known to be resin materials having high refractive indices.

Since polycarbonates have satisfactory transparency and heat resistance, polycarbonates are frequently used in optical materials. However, even for aromatic polycarbonates, their refractive indices cannot be said to be sufficiently high, and there is a demand for the development of a resin for optical materials having a higher refractive index.

An example of the resin material having a high refractive index may be a polyester-based block copolymer containing a polyester block chain adopting a fluorene skeletal structure (see, Patent Literature (hereinafter, abbreviated as PTL) 1). Furthermore, a polyimide obtainable from a diamine compound having a naphthalene skeletal structure is known (see PTL 2). These copolymers are considered to be useful in materials for forming optical devices.

CITATION LIST

Patent Literature

PTL 1
Japanese Patent Application Laid-Open No. 2009-57483
PTL 2
Japanese Patent Application Laid-Open No. 2010-70513

SUMMARY OF INVENTION

Technical Problem

However, the polyester-based block copolymer described in PTL 1 does not have sufficiently high heat resistance and a sufficiently high refractive index. Furthermore, the polyimide described in PTL 2 has insufficient transparency and insufficient molding processability. For this reason, there is a problem in that the use of optical devices obtainable by using this polyimide is restricted.

The present invention was achieved in view of such problems of the related art. That is, an object of the present invention is to provide a resin which is useful for materials that are intended to construct optical devices and the like, has a high refractive index, and is highly transparent. Another object of the present invention is to provide an optical material which has a high refractive index and is highly transparent, and an optical device.

Solution to Problem

The inventors of the present invention conducted a thorough investigation in order to achieve the objects described above, and as a result, the inventors found that a resin having a particular structure containing an acylhydrazone bond has a high refractive index, and also has a high light transmittance. Particularly, the inventors found that when a repeating unit having an acylhydrazone bond which is capable of hydrogen bonding and a benzene ring moiety containing a (thio)ether bond is contained, the density of the resin is increased, and a resin having a high refractive index is obtained. Thus, the inventors achieved the present invention.

That is, according to the present invention, there are provided a resin, an optical material, and an optical device as follows.

[1] A resin containing an acylhydrazone bond and having a number average molecular weight of 500 to 500,000, the resin having an acylhydrazone bond equivalent of 100 to 4000.

[2] The resin as described in item [1], wherein the ratio of the sum of the number of aldehyde groups and the number of acylhydrazine groups contained in the resin with respect to the number of terminal groups contained in the resin is less than 1.

[3] The resin as described in item [1] or [2], wherein at least a portion of the acylhydrazine ends are capped.

[4] The resin as described in any one items [1] to [3], containing a repeating unit represented by the following Formula (1):

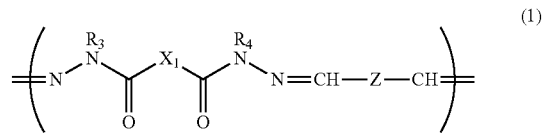

wherein in Formula (1), $X_1$ represents a divalent linking group containing atoms selected from the group consisting of C, H, N, O, S, Si, F, Cl, Br, and I, and having a molecular weight of 80 to 8,000, in which the number of atoms of the shortest molecular chain that links the carbonyl carbon atoms of the two acylhydrazone bond is 2 to 60;

$R_3$ and $R_4$ each independently represent a hydrogen group, a methyl group, or a phenyl group;

Z represents a group represented by any one of the following Formulas (2) to (6), or a saturated hydrocarbon group having 1 to 12 carbon atoms:

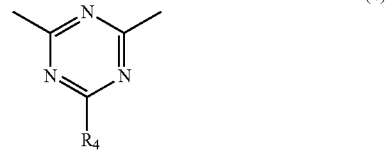

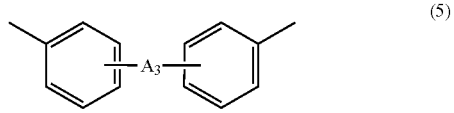

-continued (6)

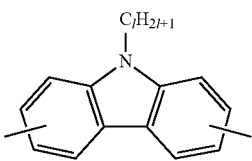

wherein in Formula (2), $A_1$ represents —CH= or —N=, while the positions of the bonding hands on the aromatic ring are the 2-position and the 6-position, or the 2-position and the 5-position with respect to $A_1$, and the aromatic ring may have a methyl group, an ethyl group or a halogen atom at the other positions;

in Formula (3), $A_2$ represents —$CH_2$—, —O—, —S—, or —N(R)— (wherein R represents a hydrogen atom, a methyl group, or an ethyl group);

in Formula (4), $R_5$ represents a hydrogen atom, a methyl group, an ethyl group, a methoxy group, an ethoxy group, a halogen atom, a methylthio group, or an ethylthio group;

in Formula (5), $A_3$ represents —$CH_2$—, —$C(CF_3)_2$—, —S—, —$C(CH_3)_2$—, —O—, —$SO_2$—, —S(=O)—, —C(=O)—, —C(=O)NH—, or —O—$C_pH_{2p}$—O— (wherein p represents an integer from 2 to 12); and in Formula (6), l represents an integer from 1 to 8.

[5] The resin as described in item [4], wherein in Formula (1), $X_1$ represents an alkylene group having 2 to 30 carbon atoms, which may be substituted.

[6] The resin as described in item [4], wherein $X_1$ in Formula (1) is represented by any one of the following Formulas (A-1) to (A-3):

(A-1)

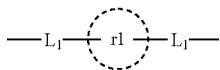

wherein in Formula (A-1), ring r1 represents an aromatic ring which may be substituted; and $L_1$ represents a single bond, or a divalent linking group composed of atoms selected from the group consisting of H, O, C, N and S and having a molecular weight of 500 or less, while two $L_1$'s may be identical with or different from each other;

(A-2)

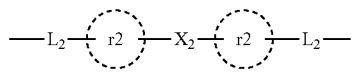

wherein in Formula (A-2), ring r2 represents an aromatic ring which may be substituted, while two ring r2's may be identical with or different from each other;

$X_2$ represents a single bond, —$CH_2$—, —$C(CF_3)_2$—, —S—, —$C(CH_3)_2$—, —O—, —$SO_2$—, —S(=O)—, —C(=O)NH—, —C(=O)—, a group represented by the following Formula (1-1), a group represented by the following Formula (1-2), or a group capable of forming a spiro bond together with two ring r2's; and $L_2$ represents a single bond, or a divalent linking group composed of atoms selected from the group consisting of H, O, C, N and S and having a molecular weight of 500 or less, while two $L_2$'s may be identical with or different from each other:

(1-1)

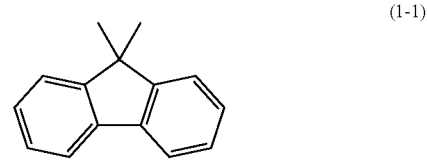

(1-2)

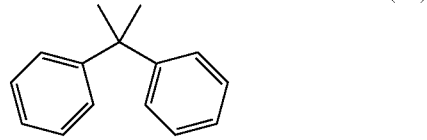

(A-3)

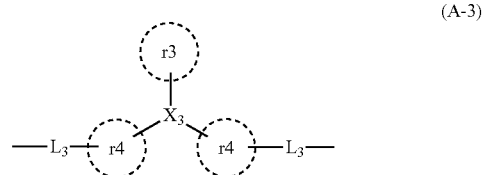

wherein in Formula (A-3), ring r3 and ring r4 each independently represent an aromatic ring which may be substituted, while two ring r4's may be identical with or different from each other;

$X_3$ represents a trivalent or tetravalent carbon atom;

when $X_3$ represents a tetravalent carbon atom, the substituent bonded to $X_3$ is any of a methyl group and a phenyl group; and $L_3$ represents a single bond, or a divalent linking group composed of atoms selected from the group consisting of H, O, C, N and S and having a molecular weight of 500 or less, while two $L_3$'s may be identical with or different from each other.

[7] The resin as described in item [6], wherein r1 in Formula (A-1) represents a naphthalene ring.

[8] The resin as described in item [6], wherein $X_2$ in Formula (A-2) represents a single bond, and r2 represents a naphthalene ring.

[9] The resin as described in item [4], wherein the repeating unit represented by Formula (1) is represented by the following Formula (1'):

(1')

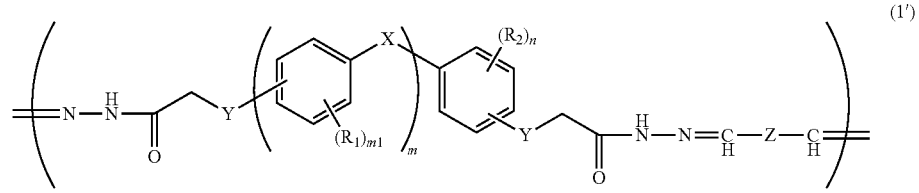

wherein in Formula (1'),

X represents any of structures selected from —CH$_2$—, —C(CF$_3$)$_2$—, —S—, —C(CH$_3$)$_2$—, —O—, —SO$_2$—, —S(=O)—, —C(=O)NH—, —C(=O)—, a group represented by the following Formula (1-1), and a group represented by the following Formula (1-2);

Y's each independently represent —O—, —CH$_2$—, or —S—;

m represents an integer from 0 to 10;

m1 and n each independently represent an integer from 0 to 4;

R$_1$ and R$_2$ each independently represent a methyl group, an ethyl group, a propyl group, a butyl group, a methoxy group, an ethoxy group, an aryl group, an aryloxy group, or a halogen group; and Z represents a group represented by any of Formulas (2) to (6) described above, or a saturated hydrocarbon group having 1 to 12 carbon atoms:

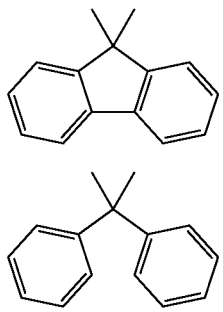

(1-1)

(1-2)

[10] The resin as described in item [9], wherein X in Formula (1') represents —CH$_2$—, —S—, or —C(CH$_3$)$_2$—.

[11] The resin as described in item [9] or [10], wherein Z in Formula (1') represents a group represented by Formula (2) or (3) described above.

[12] The resin as described in any one of items [9] to [11], wherein X and Y in Formula (1') both represent —S—.

[13] The resin as described in any one of items [3] to [12], wherein the ratio of the sum of the numbers of aldehyde groups and acylhydrazine groups contained in the resin with respect to the number of terminal groups contained in the resin is less than 1.

[14] The resin as described in any one of items [3] to [13], wherein at least a portion of acylhydrazine ends are capped.

[15] An optical material containing the resin as described in any one of items [1] to [14], and at least one additive selected from the group consisting of inorganic particles, metal particles, and ionic compounds.

[16] An optical device including the resin as described in any one of items [1] to [14].

[17] An optical device including a light emitting element, and a luminous flux control member containing the resin as described in any one of items [1] to [14] and formed in a shape capable of controlling the luminous flux emitted from the light emitting element.

[18] An organic EL device including an organic EL element, a transparent electrode layer, and a resin layer containing the resin as described in any one of items [1] to [14], in this order.

[19] A lens formed from the resin as described in any one of items [1] to [14].

Advantageous Effects of Invention

The resin of the present invention has a high refractive index and is highly transparent. Therefore, the resin of the present invention is particularly useful as an optical material, and can provide excellent optical devices.

DESCRIPTION OF EMBODIMENTS

1. As to Resin

Figure 1A:
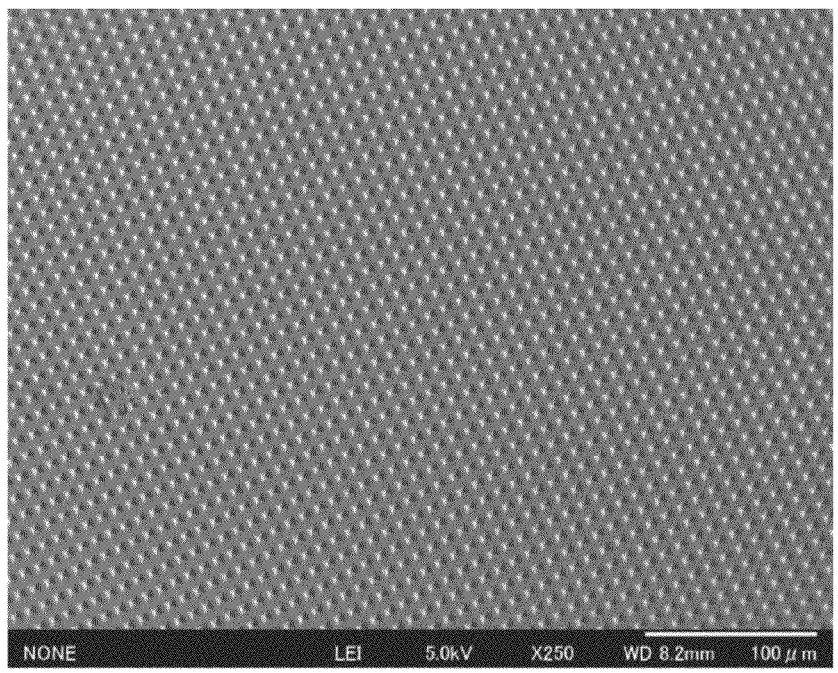
FIG. 1A is an image obtained by observing a fine structure produced in a film in Example 26, with a scanning electron microscope (SEM)

The resin of the present invention contains an acylhydrazone bond (—C(=O)—NH—N=CH—). It is speculated that when an acylhydrazone bond that is capable of hydrogen bonding is present in a repeating unit, acylhydrazone bonds may easily interact with each other due to hydrogen bonding. Furthermore, it is contemplated that as acylhydrazone bonds are brought near to each other by hydrogen bonding, the density of the resin is increased, and the refractive index is increased.

The acylhydrazone bond equivalent of the resin of the present invention is preferably 100 to 4,000, more preferably 120 to 2,000, and particularly preferably 130 to 500. When the acylhydrazone bond equivalent is greater than 100, transparency of the resin tends to increase. On the other hand, if the acylhydrazone bond equivalent is smaller than 4000, the refractive index of the resin tends to increase. The acylhydrazone bond equivalent is a value obtained by dividing the average molecular weight (Mn) of the resin by the average number of acylhydrazone bonds contained in the resin. The average number of acylhydrazone bonds contained in the resin can be calculated by, for example, NMR, titration or the like.

The number average molecular weight (Mn) of the resin of the present invention is 500 to 500,000, preferably 5,000 to 200,000, and even more preferably 25,000 to 100,000. When the number average molecular weight (Mn) is in the value range described above, the resin of the present invention exhibits satisfactory molding processability. Meanwhile, if the number average molecular weight (Mn) is too small, the resin becomes brittle, and it tends to become difficult to maintain the resin in a predetermined shape. On the other hand, if the number average molecular weight (Mn) is too large, the melt viscosity of the resin increases, and molding processability and the like tend to deteriorate. The number average molecular weight (Mn) of the resin is usually measured by gel permeation chromatography (GPC), and is calculated as a value relative to polystyrene standards. Specifically, the number average molecular weight can be a value obtained by measuring the number average molecular weight (Mn) of the resin by a gel permeation chromatography (GPC) method. For example, while columns of "Shodex (trade name)" series manufactured by Showa Denko K.K. are used, and the analysis conditions are set as follows, the number average molecular weight (Mn) can be calculated relative to polystyrene standards.

Column temperature: 40° C.
Developing solvent: DMF (dimethylformamide) (added with LiBr at a concentration of 10 mM)
Measurement flow rate: 0.6 ml/min The ratio of the sum of the numbers of aldehyde groups and acylhydrazine groups contained in the resin with respect to the number of terminal groups contained in the resin of the present invention is preferably less than 1, more preferably less than 0.3, and even more preferably less than 0.1. That is, it is preferable that the number of aldehyde groups and acylhydrazine groups present in the resin be smaller. The term terminal group as used herein means a group that is located at the ends of the main chain of the resin, and there are no limitations on the kind of the functional group. Furthermore, the main chain may be a molecular chain composed mainly of a repeating unit structure containing an acylhydrazine bond. Therefore, usually, a linear resin has two terminal groups per molecule. On the other hand, in the case of a resin having a branched structure, the resin may have two or more terminal groups per molecule. For example, when one molecule of a resin is synthesized by crosslinking two molecular chains each mainly composed of a repeating unit structure containing an acylhydrazine bond, at a site other than the terminal parts of the molecular chains, there will be four terminal parts.

For example, as described in Japanese Patent Application Laid-Open No. 57-88156 or WO 2006/003905, when a polyacylhydrazone resin is prepared by condensing a dialdehyde and a dihydrazide, the resin has aldehyde groups or acylhydrazine groups at the ends. That is, the number of the terminal groups contained in the resin becomes equal to the sum of the numbers of aldehyde groups and acylhydrazine groups, and the "ratio of the sum of the number of aldehyde groups and the number of acylhydrazine groups contained in the resin with respect to the number of terminal groups contained in the resin" becomes 1.

In this regard, in the resin of the present invention, it is preferable that these aldehyde groups or acylhydrazine groups be capped with an end-capping agent. When other functional groups (capping agent) are bonded to the aldehyde groups or acylhydrazine groups, the number of aldehyde groups and acylhydrazine groups located at the ends of the resin decreases. That is, the "ratio of the sum of the number of aldehyde groups and the number of acylhydrazine groups contained in the resin with respect to the number of terminal groups contained in the resin is less than 1."

The number of aldehyde groups and the number of acylhydrazine groups contained in the resin can be respectively determined by titration or NMR. On the other hand, the number of terminal groups contained in the resin can be determined by determining the number average molecular weight of the resin, and dividing the mass of the resin by the number average molecular weight, or the like. Usually, the number of terminal groups is a mole number that is twice the mole number of the resin.

When the resin has acylhydrazine ends, it is preferable that at least a portion of the acylhydrazine ends, that is, a portion or all of the acylhydrazine groups that are located at the ends of the resin, be capped with an end-capping agent. When the acylhydrazine ends are capped with an end-capping agent, the light transmittance is increased.

The capping ratio of the acylhydrazine ends is regulated by the amount of addition of the end-capping agent.

The amount of addition (molar amount) of the end-capping agent that caps an acylhydrazine end is preferably greater than 0% to 120%, more preferably 70% to 100%, and even more preferably 90% to 100%, relative to the molar amount of the acylhydrazine ends contained in the resin. If the amount of addition of the end-capping agent is small, the acylhydrazine ends may not be sufficiently capped. On the other hand, if the amount of addition of the end-capping agent is greater than 120%, or depending on the case, greater than 100%, the molecular chain that constitutes the resin is broken, aldehyde ends become likely to be exposed, and there is a risk that the light transmittance may rather decrease.

The end-capping agent that caps an acylhydrazine end may be any compound which reacts with an acylhydrazine group and forms an end with low reactivity. Examples of the end-capping agent include monoaldehydes, acid anhydrides, and acid chlorides. The monoaldehydes may be any of aliphatic monoaldehydes or aromatic monoaldehydes.

Examples of a monoaldehyde that caps an acylhydrazine end include benzaldehyde and 4-chlorobenzaldehyde. Examples of an acid anhydride that caps an acylhydrazine end include acetic anhydride and succinic anhydride. Among these, benzaldehyde is particularly preferred because a reactive functional group hardly remains behind after benzaldehyde reacts with the aldehyde at the end of the resin.

Furthermore, when the resin has aldehyde ends, it is also preferable that at least a portion or all of the aldehyde ends be capped with an end-capping agent. If aldehyde ends are capped, the coloration or the like of the resin at the time of heating is suppressed.

The amount of addition (molar amount) of the end-capping agent that caps an aldehyde end is preferably greater than 0% to 120%, more preferably 70% to 100%, and even more preferably 90% to 100%, relative to the molar amount of the aldehyde ends contained in the resin. If the amount of addition of the end-capping agent is small, the aldehyde ends may not be sufficiently capped. On the other hand, if the amount of addition of the end-capping agent is greater than 120%, or depending on the case, greater than 100%, the molecular chain that constitutes the resin is broken, aldehyde ends become likely to be exposed, and there is a risk that the light transmittance may rather decrease.

The end-capping agent that caps an aldehyde end may be any compound that reacts with an aldehyde group at the aldehyde end and forms an end with low reactivity. Examples of the end-capping agent include compounds having an amino group, a hydrazine group, an acylhydrazine group, or a hydroxylamine group. Furthermore, the aldehyde group may form an acetal group with an alcohol, or may also form an acetyl group with an acid anhydride. Specific examples of the end-capping agent that caps an aldehyde end include acetohydrazide, n-octanohydrazide, and stearic acid hydrazide, and among these, acetohydrazide is particularly preferred because a reactive functional group hardly remains behind after acetohydrazide reacts with the end of the resin to cap the end.

The resin of the present invention preferably contains a repeating unit represented by the following Formula (1). Meanwhile, the resin of the present invention may be a resin in which a portion of the resin is three-dimensionally crosslinked, or for example, a repeating unit represented by the following Formula (1) may be three-dimensionally crosslinked.

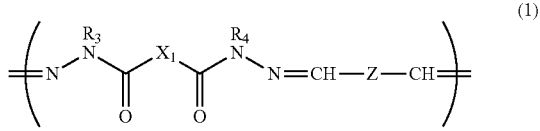

(1)

The number of the repeating unit represented by Formula (1) that is contained in the resin of the present invention is preferably 1% to 100%, and more preferably 50% to 100%, relative to the number of all the repeating units that constitute the resin. When the repeating unit represented by Formula (1) is contained at a proportion in the range described above, the refractive index of the resin increases, and light transmittance is also further increased.

There are no particular limitations on the geometric isomerism of the acylhydrazone bond in the repeating unit represented by Formula (1). For example, as indicated by the following formula, one repeating unit may contain an acylhydrazone bond that is an E-form geometric isomer and an acylhydrazone bond that is a Z-form geometric isomer. When an E-form and a Z-form of acylhydrazone bonds are contained in one repeating unit, the crystallization of the resin is suppressed, and thus the transparency of the resin increases. Furthermore, the resin of the present invention may contain a repeating unit in which two acylhydrazone bonds are all in the E-form, or a repeating unit in which two acylhydrazone bonds are all in the Z-form.

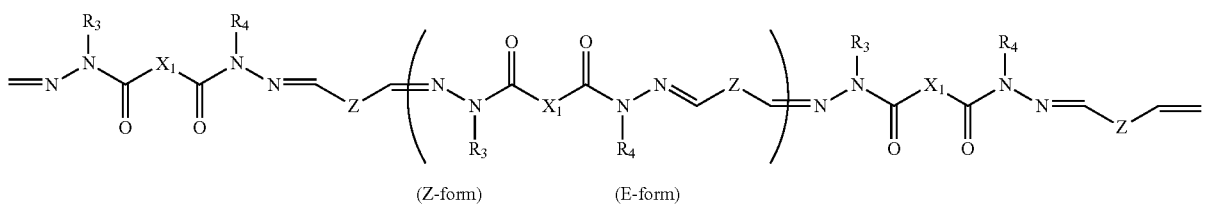

(Z-form)     (E-form)

$R_3$ and $R_4$ in Formula (1) each independently represent a hydrogen group, a methyl group, or a phenyl group. For $R_3$ and $R_4$, among others, a functional group capable of interacting with the acylhydrazone bond is preferred, and particularly a hydrogen group is preferred. When $R_3$ and $R_4$ are hydrogen groups, the resin has a high density, and the refractive index of the resin increases.

$X_1$ in Formula (1) is a divalent linking group which contains atoms selected from the group consisting of C, H, N, O, S, Si, F, Cl, Br and I, and has a molecular weight of 80 to 8,000, preferably 100 to 2,500, and more preferably 150 to 700. Also, the number of atoms that constitute the shortest molecular chain that links the carbonyl carbon atoms of the two acylhydrazone bonds is 2 to 60, and preferably 6 to 20. Depending on the structure of the repeating unit, there may be two or more methods for counting the number of atoms that are located between two carbonyl carbon atoms. In this case, the "number of atoms that constitute the shortest molecular chain" refers to the number of atoms obtainable when counted by a counting method which gives the smallest number of atoms described above. If the number of atoms that link the carbonyl carbon atoms is high, the density of the resin is likely to be low, and the refractive index is likely to be decreased.

$X_1$ in Formula (1) is preferably an alkylene group having 2 to 30 carbon atoms which may be substituted, or any one of the following Formulas (A-1) to (A-3).

When $X_1$ in Formula (1) is an alkylene group, the number of carbon atoms of the alkylene group is 2 to 30, preferably 2 to 18, and more preferably 4 to 10. The substituent that is bonded to the alkylene group may be a methyl group, an ethyl group, or a halogen group. However, in order to obtain a resin having a high refractive index, it is preferable that the group that is bonded to the alkylene group be a less bulky (small) group, or an atom which exhibits high atomic refraction. Therefore, it is preferable that the alkylene group have no substituent, or the substituent that is bonded to the alkylene group be a halogen group such as a chloro group, a bromo group, or an iodo group.

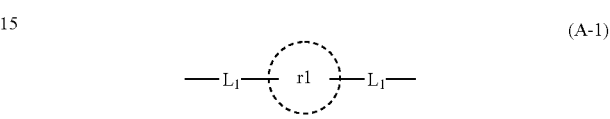

(A-1)

Ring r1 in Formula (A-1) represents an aromatic ring which may be substituted. The aromatic ring may be an aromatic hydrocarbon ring, or may be an aromatic heterocyclic ring. Examples of the aromatic ring include a benzene ring, a naphthalene ring, a furan ring, and a thiophene ring. Particularly, a naphthalene ring is preferred.

The substituent that is bonded to ring r1 of Formula (A-1) may be a methyl group, an ethyl group, or a halogen group. However, in order to obtain a resin having a high refractive index, it is preferable that the group that is bonded to ring r1 in Formula (A-1) be a less bulky (small) group, or an atom which exhibits high atomic refraction. Therefore, it is preferable that ring r1 in Formula (A-1) have no substituent, or the substituent be a halogen group such as a chloro group, a bromo group, or an iodo group.

$L_1$ in Formula (A-1) represents a single bond, or a divalent linking group composed of atoms selected from the group consisting of H, O, C, N and S, and having a molecular weight of 500 or less, and preferably 100 or less. Specific examples of $L_1$ include —S—, —O—, methylene, ethylene, propylene, butylene, oxymethylene, oxyethylene, oxypropylene, oxybutylene, thiomethylene, thioethylene, thiopropylene, thiobutylene, and carbonylene. In regard to Formula (A-1), two $L_1$'s may be identical with or different from each other.

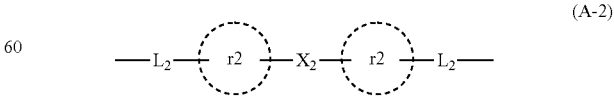

(A-2)

Ring r2 in Formula (A-2) represents an aromatic ring which may be substituted. Ring r2 may be an aromatic hydrocarbon ring, or may be an aromatic heterocyclic ring. Examples of ring r2 include a benzene ring, a naphthalene ring, an anthracene ring, a fluorene ring, a pyridine ring, a furan ring, a benzofuran ring, a thiophene ring, a benzothiophene ring, a benzothiazole ring, an indane ring, a chromane ring, an indole ring, and an a-pyrone ring. Ring r2 is preferably a benzene ring. In regard to Formula (A-2), two ring r2's may be identical with or different from each other.

The substituent that is bonded to ring r2 may be a methyl group, an ethyl group, or a halogen group. However, in order to obtain a resin having a high refractive index, it is preferable that the group that is bonded to ring r1 in Formula (A-2) be a less bulky (small) group, or an atom which exhibits high atomic refraction. Therefore, it is preferable that ring r1 in Formula (A-2) have no substituent, or the substituent be a halogen group such as a chloro group, a bromo group, or an iodo group.

$L_2$ in Formula (A-2) represents a single bond, or a divalent linking group composed of atoms selected from the group consisting of H, O, C, N and S and having a molecular weight of 500 or less, and preferably 100 or less. Specific examples of $L_2$ include —S—, —O—, methylene, ethylene, propylene, butylene, oxymethylene, oxyethylene, oxypropylene, oxybutylene, thiomethylene, thioethylene, thiopropylene, thiobutylene, and carbonylene. In Formula (A-2), two $L_2$'s may be identical with or different from each other.

$X_2$ in Formula (A-2) represents any of a single bond, —CH$_2$—, —C(CF$_3$)$_2$—, —S—, —C(CH$_3$)$_2$—, —O—, —SO$_2$—, —S(=O)—, —C(=O)NH—, —C(=O)—, a group represented by the following Formula (1-1), a group represented by the following Formula (1-2), and a group which forms a spiro bond together with two ring r2's.

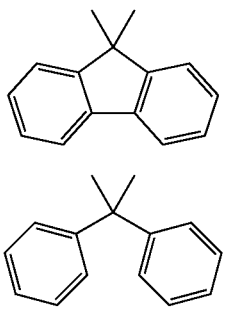

(1-1)

(1-2)

When $X_2$ in Formula (A-2) is a group which forms a spiro bond together with two ring r2's, two ring r2's and $X_2$ form, for example, a structure represented by any of the following Formulas (2-1) to (2-3):

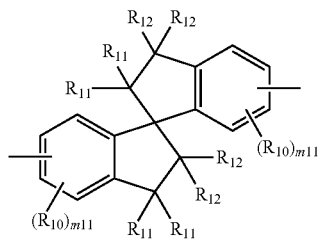

(2-1)

$R_{11}$'s and $R_{12}$'s in Formula (2-1) each independently represent a hydrogen atom, a halogen atom, an alkyl group, an alkenyl group, an alkynyl group, or an aryl group. $R_{11}$'s and $R_{12}$'s are each preferably a hydrogen atom, a methyl group, or a phenyl group. Furthermore, four $R_{11}$'s may be identical with or different from each other. Similarly, four $R_{12}$'s may be identical with or different from each other.

$R_{10}$ in Formula (2-1) is the same as the substituent that is bonded to ring r2 in Formula (A-2), and $R_{10}$'s each independently represent a methyl group, an ethyl group, or a halogen group. m11 in Formula (2-1) each independently represent an integer from 0 to 3, preferably 0 to 2, and more preferably 0.

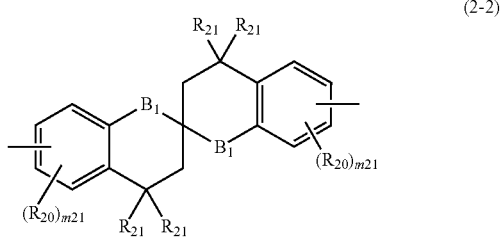

(2-2)

$R_{21}$'s in Formula (2-2) each independently represent a hydrogen atom, a halogen atom, an alkyl group, an alkenyl group, an alkynyl group, or an aryl group. $R_{21}$'s are each preferably a hydrogen atom, a methyl group, or a phenyl group. Furthermore, four $R_{21}$'s may be identical with or different from each other.

$B_1$ in Formula (2-2) represents —O— or —S—. $B_1$ is preferably —S—.

$R_{20}$ in Formula (2-2) is the same as the substituent that is bonded to ring r2 in Formula (A-2), and $R_{20}$'s each independently represent a methyl group, an ethyl group, or a halogen group. m21's in Formula (2-2) each independently represent an integer from 0 to 3, preferably 0 to 2, and more preferably 0.

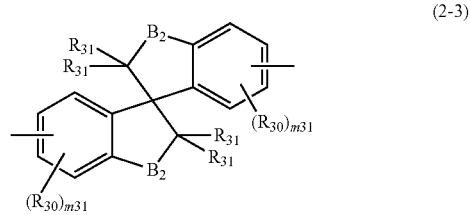

(2-3)

$R_{31}$'s in Formula (2-3) each independently represent a hydrogen atom, a halogen atom, an alkyl group, an alkenyl group, an alkynyl group, or an aryl group. $R_{31}$'s are each more preferably a hydrogen atom, a methyl group, or a phenyl group. Furthermore, four $R_{31}$'s may be identical with or different from each other.

$B_2$ in Formula (2-3) represents —O— or —S—. $B_2$ is preferably —S—.

$R_{30}$ in Formula (2-3) is the same as the substituent that is bonded to ring r2 in formula (A-2), and $R_{30}$'s each independently represent a methyl group, an ethyl group, or a halogen group. m31's in Formula (2-3) each independently represent an integer from 0 to 3, preferably 0 to 2, and more preferably 0.

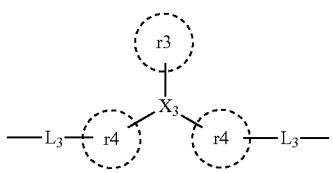
(A-3)

Ring r3 and ring r4 in Formula (A-3) each independently represent an aromatic ring which may be substituted. Ring r4 may be an aromatic hydrocarbon ring, or may be an aromatic heterocyclic ring. Examples of ring r4 include a benzene ring, a naphthalene ring, an anthracene ring, a fluorene ring, a cyclohexane ring, a cyclopentane ring, a pyridine ring, a furan ring, a benzofuran ring, a thiophene ring, a benzothiophene ring, a benzothiazole ring, an indane ring, a chromane ring, an indole ring, and an a-pyrone ring. Ring r4 is preferably a benzene ring. Two ring r4's may be identical with or different from each other.

Ring r3 in Formula (A-3) may be an aromatic hydrocarbon ring, or may be an aromatic heterocyclic ring. Examples of the aromatic ring include a benzene ring, a naphthalene ring, a furan ring, and a thiophene ring.

The substituent that is bonded to ring r3 or r4 in Formula (A-3) may be a methyl group, an ethyl group, or a halogen group. However, in order to obtain a resin having a high refractive index, it is preferable that the group that is bonded to ring r1 in Formula (A-2) be a less bulky (small) group, or an atom which exhibits high atomic refraction. Therefore, it is preferable that ring r1 in Formula (A-2) have no substituent, or the substituent be a halogen group such as a chloro group, a bromo group, or an iodo group.

$X_3$ in Formula (A-3) represents a trivalent or tetravalent carbon atom. When $X_3$ is a tetravalent carbon atom, the substituent that is bonded to $X_3$ may be a methyl group or a phenyl group.

$L_3$ in Formula (A-3) represents a single bond, or a divalent linking group composed of atoms selected from the group consisting of H, O, C, N and S and having a molecular weight of 500 or less, and preferably 100 or less. Specific examples of $L_3$ include —S—, —O—, methylene, ethylene, propylene, butylene, oxymethylene, oxyethylene, oxypropylene, oxybutylene, thiomethylene, thioethylene, thiopropylene, thiobutylene, and carbonylene. In regard to Formula (A-3), two $L_3$'s may be identical with or different from each other.

Z in Formula (1) represents a group represented by any one of the following Formulas (2) to (6), or a saturated hydrocarbon group having 1 to 12 carbon atoms.

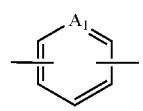
(2)

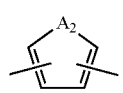
(3)

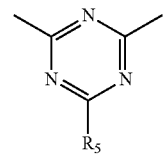
(4)

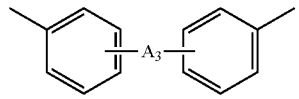
(5)

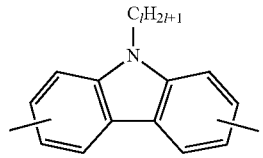
(6)

$A_1$ in Formula (2) represents —CH= or —N=. The positions of the bonding hands on the aromatic ring are the 2-position and the 6-position, or the 2-position and the 5-position with respect to $A_1$, and the other positions on the aromatic ring may be each occupied by a methyl group, an ethyl group or a halogen atom.

$A_2$ in Formula (3) represents —$CH_2$—, —O—, —S—, or —N(R)— (wherein R represents a hydrogen atom, a methyl group, or an ethyl group). Among them, $A_2$ in Formula (3) is preferably —$CH_2$—. It is because the hue of the resin becomes satisfactory. The phrase "hue of the resin becomes satisfactory" means that the resin tends to have high transparency.

$R_5$ in Formula (4) represents a hydrogen atom, a methyl group, an ethyl group, a methoxy group, an ethoxy group, a halogen atom, a methylthio group, or an ethylthio group. Among them, $R_5$ in Formula (4) is preferably a hydrogen atom, a halogen atom, or a methylthio group.

$A_3$ in Formula (5) represents —$CH_2$—, —$C(CF_3)_2$—, —S—, —$C(CH_3)_2$—, —O—, —$SO_2$—, —S(=O)—, —C(=O)—, —C(=O)NH—, or —O—$C_pH_{2p}$—O— (wherein p represents an integer from 2 to 12). When $A_3$ in Formula (5) is —O— or —S—, it is preferable because the refractive index of the resin increases.

"p" in the formula: "—O—$C_pH_{2p}$—O—" is preferably an integer from 2 to 18, and more preferably an integer from 2 to 6.

1 in Formula (6) represents an integer from 1 to 8, and more preferably 1 to 3. "—$C_lH_{2l+1}$" in Formula (6) also includes a branched hydrocarbon group such as a 2-ethylhexyl group.

When Z in Formula (1) is a saturated hydrocarbon group, the number of carbon atoms is 1 to 12, and preferably 1 to 5. Specific examples of the saturated hydrocarbon group include a methylene group and an ethylene group.

The repeating unit represented by Formula (1) is preferably a repeating unit represented by the following Formula (1') or a repeating unit represented by the following Formula (1"). In the case of the repeating unit represented by Formula (1') and the repeating unit represented by Formula (1"), too, one repeating unit may contain an acylhydrazone bond that is an E-form geometric isomer and an acylhydrazone bond that is a Z-form geometric isomer.

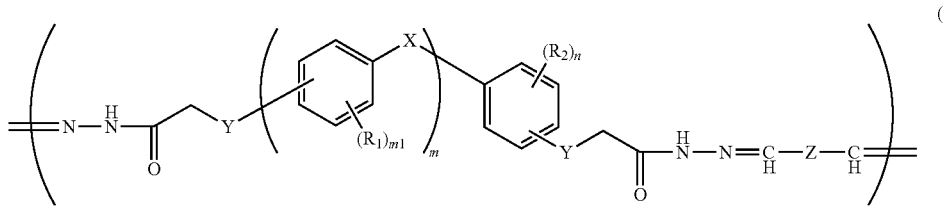

wherein in Formula (1'), X represents any structure selected from —CH$_2$—, —C(CF$_3$)$_2$—, —S—, —C(CH$_3$)$_2$—, —O—, —SO$_2$—, —S(=O)—, —C(=O)NH—, —C(=O)—, Formula (1-1) and Formula (1-2); Y's each independently represent —O—, —CH$_2$—, or —S—; m represents an integer from 0 to 10; m1 and n each independently represent an integer from 0 to 4; R$_1$ and R$_2$ each independently represent a methyl group, an ethyl group, a propyl group, a butyl group, a methoxy group, an ethoxy group, an aryl group, or a halogen group; and Z represents a group represented by any one of Formulas (2) to (6), or a saturated hydrocarbon group having 1 to 12 carbon atoms, and preferably 1 to 5 carbon atoms.

In Formula (1'), X represents —CH$_2$—, —C(CF$_3$)$_2$—, —S—, —C(CH$_3$)$_2$—, —O—, —SO$_2$—, —S(=O)—, —C(=O)NH—, or —C(=O)—. If X in Formula (1') is a relatively less bulky group, the density of the resin is likely to be high, and the refractive index tends to increase. Therefore, X in Formula (1') is preferably —CH$_2$—, —S— or —C(CH$_3$)$_2$—, and more preferably —S—.

Y's in Formula (1') each independently represent —O—, —CH$_2$— or —S—. Above all, it is preferable that Y's be all —O— or —S—, because the refractive index of the resin becomes higher. It is because when Y in Formula (1') is —O— or —S—, the electron density of the resin increases.

m in Formula (1') represents an integer from 0 to 10. In order to further increase the refractive index of the resin, m is preferably an integer from 0 to 10, and more preferably an integer from 1 to 4. Furthermore, m1 and n in Formula (1') each independently represent an integer from 0 to 4. In order to obtain a resin having a high refractive index, it is preferable not to introduce many substituents into the benzene ring in Formula (1'), so as the increase the resin density and to increase the refractive index. Therefore, m1 and n in Formula (1') are each independently preferably an integer from 0 to 2, more preferably 0 or 1, and particularly preferably 0.

R$_1$ and R$_2$ in Formula (1') each independently represent a hydrogen atom, a methyl group, an ethyl group, or a halogen group. However, in order to obtain a resin having a high refractive index, the group that is introduced into the benzene ring in Formula (1') is preferably a less bulky (small) group. Therefore, R$_1$ and R$_2$ in Formula (1') are preferably hydrogen atoms.

Z in Formula (1') represents a group represented by Z in Formula (1); that is, a group represented by any one of Formulas (2) to (6), or a hydrocarbon group having 1 to 5 carbon atoms, and among them, Z is preferably a group represented by Formula (2) or (3), because the refractive index of the resin increases. On the other hand, when Z in Formula (1') is a "hydrocarbon group having 1 to 5 carbon atoms," it is preferable because flexibility and molding processability of the resin become satisfactory. Particularly, when Z in Formula (1') is a group represented by Formula (2) or (3), it is preferable that X and Y in Formula (1') be all —S—, because the refractive index of the resin markedly increases.

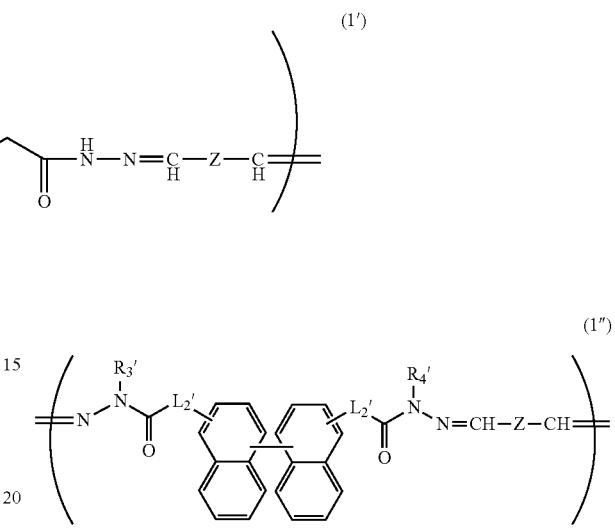

In Formula (1"), R$_3$' and R$_4$' represent the groups represented by R$_3$ and R$_4$ in Formula (1); that is, each independently represent a hydrogen group, a methyl group or a phenyl group. For R$_3$' and R$_4$', among others, a functional group capable of interacting with an acylhydrazone bond is preferred, and particularly, a hydrogen group is preferred. When R$_3$' and R$_4$' are hydrogen groups, the resin has a high density, and the refractive index of the resin increases.

Z in Formula (1") represents the groups represented by Z in Formula (1); that is, a group represented by any one of Formulas (2) to (6), or a hydrocarbon group having 1 to 5 carbon atoms. Among them, it is preferable that Z represent a group represented by Formula (2) or (3), because the refractive index of the resin increases. On the other hand, when Z in Formula (1") is "a hydrocarbon group having 1 to 5 carbon atoms", it is preferable because flexibility and molding processability of the resin become satisfactory.

L$_2$' in Formula (1") may be the same as L$_2$ in the case where X$_1$ in Formula (1) represents Formula (A-2). That is, L$_2$' may be —S—, —O—, methylene, ethylene, propylene, butylene, oxymethylene, oxyethylene, oxypropylene, oxybutylene, thiomethylene, thioethylene, thiopropylene, thiobutylene, carbonylene, or the like. In Formula (1"), two L$_2$'s may be identical with or different from each other.

Examples of the repeating unit other than the repeating unit represented by Formula (1), which is contained in the resin of the present invention, include repeating units derived from monomers or oligomers of polyamides, polyesters, polyimides, polyurethanes, polycarbonates, polyolefins and acryls, which have an aldehyde group, a hydrazine group, an amine group, a carboxylic acid group, an isocyanate group, an acid anhydride group or the like at the end, or having the aforementioned functional group bonded to the end.

The refractive index ($n_D^{25}$) of the resin of the present invention for a wavelength of 589 nm at 25° C. is usually 1.65 to 1.80, and more preferably 1.70 or more. As such, the refractive index of the resin of the present invention is higher as compared with the refractive index of conventional resins for high refractive index applications, including polycarbonates. Therefore, the resin of the present invention is suitable for a constituent material for optical devices and the like that are required to have high refractive indices. The refractive index ($n_D^{25}$) of a resin is measured using an Abbe refractometer according to JIS K-7142 A method (a method of using an Abbe refractometer).

The refractive index and the density are correlated to a certain extent. Therefore, the resin of the present invention having a high refractive index also has a density that is high to some extent. Specifically, the density of the resin of the present invention is usually 1.30 g/cm$^3$ to 1.80 g/cm$^3$, preferably 1.40 g/cm$^3$ to 1.80 g/cm$^3$, and more preferably 1.50 g/cm$^3$ to 1.80 g/cm$^3$.

The resin of the present invention has high transparency. Specifically, the total light transmittance of the resin of the present invention to visible light is usually 80% to 90%, and preferably 85% to 90%. Therefore, the resin of the present invention is suitable as a constituent material for optical devices and the like that are required to have high transparency. The total light transmittance of a resin to visible light is measured according to JIS K7105. Specifically, the total light transmittance for visible light wavelengths (380 nm to 780 nm) is measured by using a haze meter.

2. As to Method for Producing Resin

As described above, one major feature of the resin of the present invention is that the resin has an acylhydrazone bond in its repeating unit. Regarding the method for producing such a resin of the present invention having an acylhydrazone bond, for example, (i) a method of polycondensing a dialdehyde compound and a dihydrazide compound, and polymerizing the product while forming an acylhydrazone bond; and (ii) a method of polymerizing a monomer which already contains an acylhydrazone bond, may be used. Hereinafter, the method for producing the resin of the present invention will be explained by taking the (i) method of polycondensing a dialdehyde compound and a dihydrazide compound, and polymerizing the product while forming an acylhydrazone bond, as an example. Meanwhile, the method for producing the resin of the present invention is not intended to be limited to the method that will be described below.

An example of the production scheme of a resin containing a repeating unit represented by Formula (1') will be described below. Meanwhile, X, Y, Z, R$_1$, R$_2$, m, n and m1 in the following Formulas (A) and (C) to (E) have the same meanings as X, Y, Z, R$_1$, R$_2$, m, n and m1 in Formula (1'), respectively. Furthermore, Hal in the following Formula (B) represents a halogen atom, and R$_A$ in the following Formulas (B) and (C) represent a lower alkyl group (a methyl group, an ethyl group or the like).

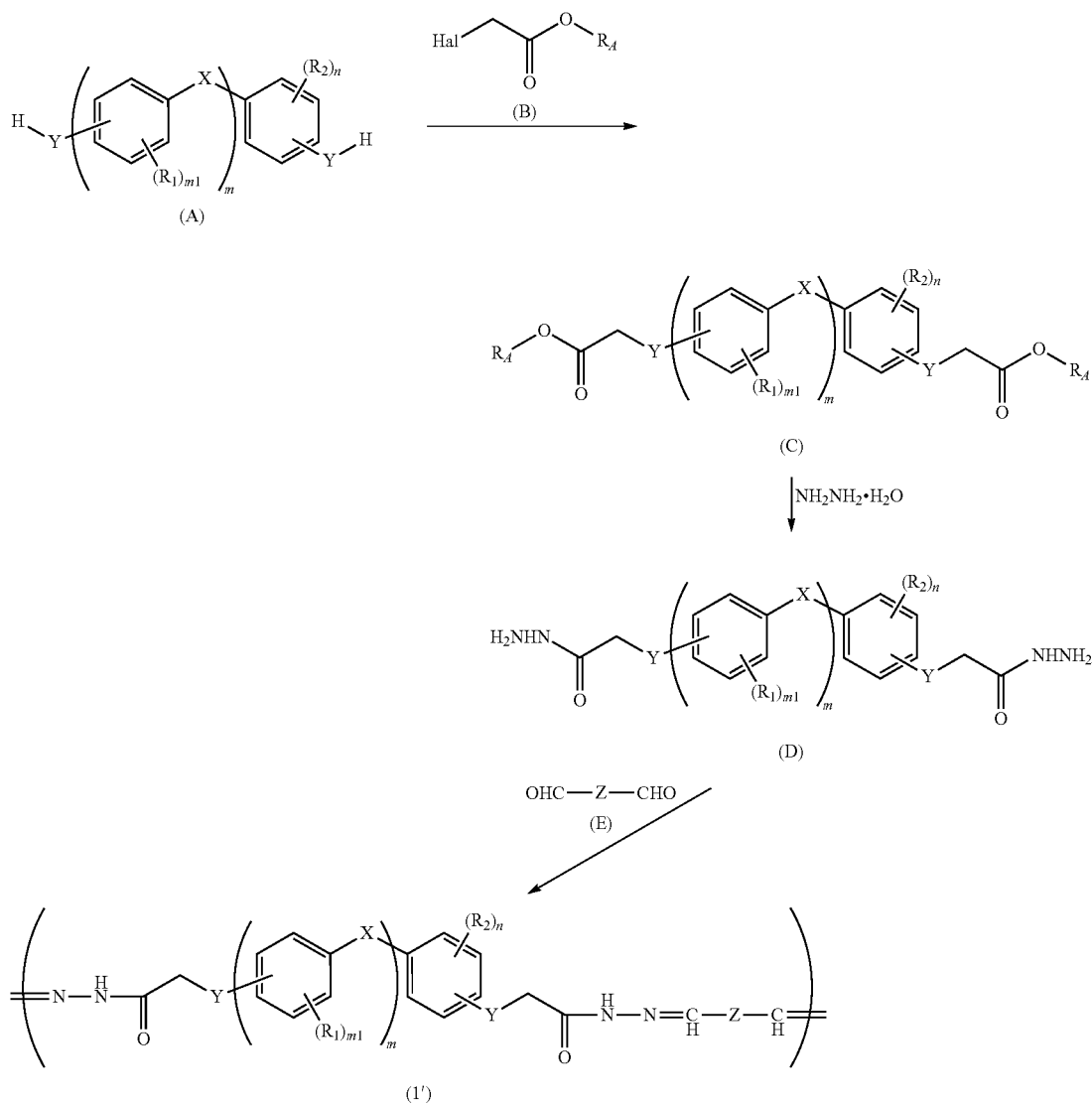

First, a diphenol (or a dithiophenol) compound represented by Formula (A) is allowed to react with a halogenated acetic acid ester represented by Formula (B), and thus a diester compound (or a dithioester compound) represented by Formula (C) is obtained. Meanwhile, the aforementioned reaction may be carried out according to a general method, for example, under basic conditions. Subsequently, the diester compound (or the dithioester compound) represented by Formula (C) thus obtained is allowed to react with a hydrazine monohydrate, and thus a dihydrazide compound represented by Formula (D) is obtained.

Thereafter, the dihydrazide compound represented by Formula (D) thus obtained and a dialdehyde compound represented by Formula (E) are polycondensed in the presence of an acid catalyst or the like that is added according to necessity, and thereby a resin of the present invention represented by Formula (1') can be obtained. By adjusting the ratio of used moles of the dialdehyde compound (Formula (E)) and the dihydrazide compound (Formula (D)), the number average molecular weight (Mn) of the resin thus obtainable can be regulated. For example, when the molar ratio of the dialdehyde compound and the dihydrazide compound is set to "dialdehyde compound"/"dihydrazide compound"=0.75 to 1.25, the number average molecular weight (Mn) of the resin thus obtainable can be adjusted to the range of 500 to 500,000.

Polycondensation between the dialdehyde compound and the dihydrazide compound is described in, for example, Japanese Patent Application Laid-Open No. 2007-269819. Furthermore, the dihydrazide compounds represented by the following Formulas (8), (14) and (18) that can serve as production intermediates of the resin of the present invention are disclosed in Japanese Patent Application Laid-Open No. 4-117354 (Formula (8) described below); Indian Journal of Chemistry, Section B: Organic Chemistry including Medicinal Chemistry (1990), 29B, 793-796, Journal of Indian Chemical Society (1989), 66, 113-115, and Journal of Indian Chemical Society (1988), 65, 782-783 (Formula (14) described below); Journal of Applied Polymer Science (1985), 30, 3283-3296, and Journal of Applied Polymer Science (1977), 21, 1469-1477 (Formula (18) described below).

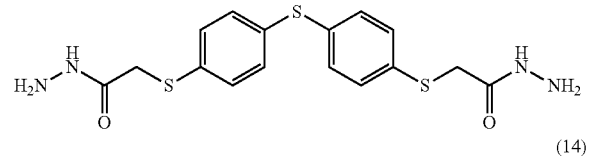

(8)

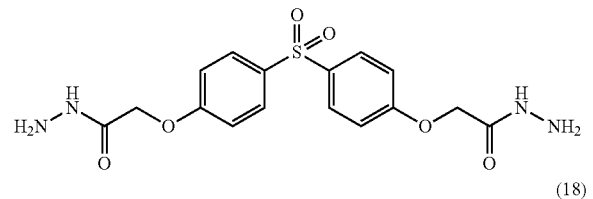

(14)

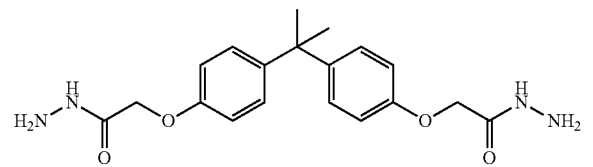

(18)

3. As to Optical Material and Optical Device

As described above, since the resin of the present invention has a high refractive index and also has high transparency, the resin of the present invention is suitable as a material for members that constitute an optical device (optical material). The optical material may be composed of, for example, only a resin, or may be composed of a resin composition containing a resin. That is, in the optical material, conventionally used additives are incorporated as necessary, as components other than the resin described above. Examples of the additive include a filler, an ionic compound, a plasticizer, a softening agent, a colorant, a dispersant, a mold releasing agent, a stabilizer, an antistatic agent, a flame retardant, an anti-blocking agent, and a crystal nucleating agent. These additives can be used singly or in combination of two or more kinds.

Specific examples of the filler include oxide fine particles of silica, talc, $TiO_2$, ZnO, CdO, PbO, $Sb_2O_5$, and the like; inorganic particles of metal sulfides, metal selenides, metal tellurides, and the like; metal particles of titanium, zirconium and the like; and fibrous fillers such as glass fibers and carbon fibers. Specific examples of the metal sulfides include CdS, ZnS, PdS, and HgS; specific examples of metal selenides include CdSe, ZnSe, HgSe, and SbSe; and specific examples of metal tellurides include CdTe. An ionic compound refers to a compound that generates a metal ion.

Specific examples of the stabilizer include oxidation inhibitors such as a hindered phenol-based oxidation inhibitor, a phosphorus-based oxidation inhibitor, a sulfur-based oxidation inhibitor, and an amine-based oxidation inhibitor; an ultraviolet absorber; and a thermal stabilizer.

Regarding the mold releasing agent, any compound which gives a mold releasing effect and does not impair the properties such as transparency of the resin, can be used. As the mold releasing agent that can be used in the present application, for example, surfactants may be used. Surfactants are roughly classified into ionic surfactants and nonionic surfactants, and ionic surfactants are further classified into anionic surfactants and cationic surfactants. In the present invention, among these, anionic surfactants are particularly preferred, and sulfuric acid ester-based, sulfonic acid ester-based, and phosphoric acid ester-based surfactants can be used as mold releasing agents. Furthermore, even among these, phosphoric acid ester-based surfactants are preferred, and particularly, acidic phosphoric acid ester-based anionic surfactants are preferred. These mold releasing agents may be used singly, or two or more kinds may be used as mixtures.

The amount of addition of the mold releasing agent in the case of incorporating the aforementioned mold releasing agents into optical materials, is usually 0.01 parts to 0.2 parts by mass, preferably 0.01 parts to 0.1 parts by mass, and more preferably 0.03 parts to 0.1 parts by mass, relative to 100 parts by mass of the resin. When the amount of addition is in the range described above, sufficient mold releasing properties can be obtained without impairing the transparency of the resin.

The amount of additives other than the mold releasing agent that are contained in the optical material is appropriately set depending on the kind, use and the like of the optical device to be produced; however, the amount is usually 0.01 parts to 100 parts by mass, preferably 0.1 parts to 50 parts by mass, and more preferably 0.5 parts to 30 parts by mass, relative to 100 parts by mass of the resin.

In addition, in the optical material, "other resins" other than the resin of the present invention may be incorporated as necessary, to the extent that the effect of the present invention is not impaired. Examples of the "other resins" include thermoplastic resins such as polyolefins, polystyrene, polyvinyl chloride, polyvinyl acetate, polyvinyl alcohol, polyacrylates, polyacetals, polycarbonates, fluororesins, polyamides, polyarylsulfone, polyaryl ether ketone, and polyaryl sulfide; and thermosetting resins such as phenolic resins, furan resins, urea resins, melamine resins, epoxy resins, unsaturated polyester resins, urethane-based resins, silicone resins, and polyimide-based resins. These "other resins" can be used singly, or two or more kinds can be used in combination.

The amount of the "other resins" that are incorporated in the optical material is appropriately set depending on the kind, use and the like of the optical device to be produced; however, the amount is usually about 0.01 parts to 50 parts by mass, preferably 0.05 parts to 15 parts by mass, and more preferably 0.1 parts to 10 parts by mass, relative to 100 parts by mass of the resin.

Members for optical devices can be produced by molding the resin described above, or an optical material containing this resin (resin composition) by conventionally used molding methods such as, for example, extrusion molding, injection molding, blow molding, calendar molding, press molding, and vacuum molding. Specific examples of the members for optical devices obtainable in this manner include an organic EL light extraction layer, a light waveguide, an optical fiber, an antireflective film, an optical lens, and a prism.

Furthermore, an optical device may include, for example, a product obtained by forming a fine structure intended for diffusion, reflection or collection of light on one surface or both surfaces of a film or sheet formed from the resin of the present invention or an optical material containing this resin (resin composition) that has been extrusion molded. This fine structure may be such that identical patterns in a convex form or a concave form are continuously formed on a film or a sheet, or plural different pattern units in a convex form or a concave form may be repeatedly formed. There are no particular limitations on the pattern shape in a convex form or a concave form. For example, the pattern shape may be a structure in which a convex portion is formed into a pillar shape, a conical shape, a hemispherical shape or the like, or may be a structure in which a concave portion is formed into a hemispherical shape, a conical shape, or a pyramidal shape. The pitch between the respective patterns can be arbitrarily selected, but usually, the pitch is preferably in the range of 100 nm to 1 mm. Furthermore, the height of concavo-convexity can also be arbitrarily selected, but usually, the height is preferably in the range of 100 nm to 1 mm.

The method for forming the fine structure on the surface of a film or a sheet formed from the resin of the present invention or an optical material containing this resin (resin composition) is not particularly limited, and the formation of the fine structure can be carried out by various known methods. For example, the fine structure can be formed by compressing a sheet formed from the resin that has been extruded from an extrusion molding machine, between a transfer roll having a desired reversal pattern formed thereon and a nip roll, and thereby transferring the desired pattern on the sheet. In this method, a fine structure can be continuously formed on a sheet by adjusting the extrusion speed of the resin and the rotation speed of the transfer roll to an equal speed.

Furthermore, the fine structure described above may be formed by laminating sheets of films or sheets formed from the resin of the present invention or a resin composition containing this resin, with a transfer stamper having a desired reversal pattern formed thereon, and subjecting the laminate to thermal transfer press molding. The conditions such as transfer temperature and pressure at the time of thermal transfer press molding can be appropriately selected in accordance with the thermal properties of the resin. For example, the resin is heated to a temperature higher by 10° C. to 100° C., and preferably to a temperature higher by 20° C. to 40° C., than the glass transition temperature of the resin, and in a state in which the elastic modulus of the resin has been brought to about 0.1 MPa to 50 MPa, the resin can be transfer molded at a pressure of 1 MPa to 10 MPa, and preferably 2 MPa to 10 MPa.

The film or sheet on which the fine structure has been formed can be used as a light diffusion film, a polarizing reflective film, a brightness enhancing film or the like of optical devices.

Furthermore, the resin of the present invention, or an optical material containing this resin (resin composition) also has excellent adhesiveness to metal layer such as an ITO layer. Therefore, the resin or the optical material of the present invention can also be used as a wiring board or the like for various optical devices.

When a mold releasing agent is not added to the resin of the present invention or an optical material containing this resin (resin composition), films or sheets formed from these have excellent adhesiveness to various substrates, and particularly excellent adhesiveness to metal plates and resin substrates. Therefore, the films or sheets can be suitably used for applications of adhesive materials having high refractive index properties, laminate materials, and the like.

On the other hand, a mold releasing agent is added to the resin of the present invention or an optical material containing this resin (resin composition), detachment between the films or sheets formed from the resin or the optical material and various substrates become satisfactory. Therefore, the films or sheets can be suitably used in applications such as protective films and peeling films.

Furthermore, the resin of the present invention may be used for the application of sealing member for organic EL devices. The structure of an organic EL device may be a top emission type, or may be a bottom emission type. In the following, the case where the resin of the present invention is used as a sealing member in an organic EL device having a top emission structure will be explained. The structure of an organic EL device having a top emission structure may be a structure including a display substrate on which an organic EL element and a transparent electrode are disposed; a counter substrate that forms a pair with the display substrate; and a sealing member that is interposed between the display substrate and the counter substrate and surface-seals the organic EL element, that is, a structure in which a substrate, an organic EL element, a transparent electrode layer, a sealing member, and a counter substrate are laminated in this order. The resin of the present invention is such that a cured product of the resin has a high refractive index, and has a high light transmittance. Therefore, when the resin of the present invention is used as the material of the sealing member, high light extraction efficiency of the organic EL device is obtained. Furthermore, the resin of the present invention has a refractive index close to the refractive index of a transparent electrode layer (ITO or the like). That is, since light reflection at the interface of a transparent electrode layer and a sealing member can be suppressed, the light extraction efficiency from the organic EL device becomes very satisfactory.

Furthermore, the resin of the present invention may be a material for a luminous flux control member of an optical device which includes a light emitting element, and a member for controlling the directivity of luminous flux emitted from the light emitting element. For example, light from an LED chip has high directivity. Thus, in an optical device using an LED chip as a light source, a luminous flux control member for diffusing light to a desired direction, or refracting luminous flux may be provided around the LED chip. The luminous flux control member may be a lens-shaped member having concavo-convexity on the surface, or the like. Such a luminous flux control member is generally produced by molding an epoxy resin with a mold.

However, since an epoxy resin is a curable resin, there is a problem in that it is difficult to mold the epoxy resin to a desired shape. On the contrary, since the resin of the present invention is a thermoplastic resin, the resin can be easily molded. Furthermore, the resin of the present invention produces a cured product having a high refractive index and a high light transmittance, and the molding processability of the resin is also satisfactory. Therefore, when the resin of the present invention is used as a material of a luminous flux control member, a luminous flux control member having a high light transmittance can be molded into a desired shape.

The resin of the present invention can also be used as a material for lenses such as a convex lens or a concave lens. The resin of the present invention has a high refractive index, and also has a high transmittance. Furthermore, the glass transition temperature (Tg) is relatively high, and the temperature dependency of the linear expansion coefficient or the refractive index is low. Thus, the resin can be suitably used in applications where precise optical information processing is required.

EXAMPLES

Hereinafter, the present invention will be specifically described by way of Examples, but the present invention is not intended to be limited to these Examples. In addition, the methods for measuring various properties will be described below.

[$^1$H-NMR and $^{13}$C-NMR]

A test material was dissolved in deuterated dimethyl sulfoxide (DMSO) or deuterated chloroform, and $^1$H-NMR and $^{13}$C-NMR of the test material were measured using a measuring apparatus having a resolution of 270 MHz. The measurement was carried out with EX-270 manufactured by JEOL, Ltd. Furthermore, tetramethylsilane (about 0.03%) was added to the test material, and this was used as a reference material.

[CHN Elemental Analysis]

A CHN elemental analysis of a test material was carried out using an organic trace element analysis apparatus (trade name: "2400 II fully automated element analysis apparatus") manufactured by PerkinElmer, Inc.

[Mass Analysis]

A mass analysis (FD-MS) of a test material (low molecular weight compound) was carried out using a gas chromatography time-of-flight mass spectrometer (trade name: "JMS-T100GC" AccuTOF GC") manufactured by JEOL, Ltd.

[GPC]

The number average molecular weight (Mn) of a test material (resin) was measured by a gel permeation chromatography (GPC) method. The number average molecular weight (Mn) was calculated relative to polystyrene standards, using columns of trade name: "Shodex" series manufactured by Showa Denko K.K. The analysis conditions were as follows.

Column temperature: 40° C.

Developing solvent: DMF (dimethylformamide) (added with LiBr at a concentration of 10 mM)

Measurement flow rate: 0.6 ml/min

[Glass Transition Temperature]

Measurement was carried out according to JIS K7121 using a differential scanning calorimetric measuring apparatus (trade name: "DSC-1") manufactured by PerkinElmer, Inc., under the conditions of a rate of temperature increase of 10° C./min, and thus a melting curve of a resin was produced. From the melting curve thus produced, the glass transition temperature (Tg) of the resin was determined.

[1% Weight Loss Temperature and 5% Weight Loss Temperature]

The 1% weight loss temperature ($T_{dec}$ 1 wt (° C.)) and the 5% weight loss temperature ($T_{dec}$ 5 wt (° C.)) of a resin were measured using a TG/DTA simultaneous measuring apparatus (trade name: "DTG-60") manufactured by Shimadzu Corp.

[Total Light Transmittance]

The total light transmittance (%) of a resin to visible light (wavelength: 380 nm to 780 nm) was measured according to JIS K7105 using a haze meter, TCHIIIDPK (manufactured by Tokyo Denshoku Co., Ltd.). The thickness of the measurement sample was set to 100 μm.

[Elastic Modulus]

The elastic modulus (%) of a resin was measured using a dynamic viscoelasticity measuring apparatus (trade name: "RSA-HI") manufactured by TA Instruments, Inc. under the conditions of a rate of temperature increase of 3° C./min.

[Tensile Strength and Tensile Elongation]

A film produced was cut to a size of 30×10 [mm], and the tensile strength and tensile elongation at 25° C. were measured using a tensile strength tester (Instron 1123 manufactured by Instron, Inc.).

[Refractive Index]

The refractive index ($n_D^{25}$) of a resin for a wavelength of 589 nm at 25° C. was measured according to the method of JIS K-7142 A (method of using an Abbe refractometer) using an Abbe refractometer (trade name: "DR-M4/1550") manufactured by Atago Co., Ltd.

Synthesis Example 1

100.0 g of 4,4'-thiobisbenzenethiol, 123.4 g of methyl bromoacetate, and 500 ml of dimethylformamide (DMF) were mixed. While the mixture was maintained at 20° C. or lower, 220.8 g of potassium carbonate was added thereto, and a suspension thus obtained was allowed to react for 3 hours at room temperature. After completion of the reaction, a precipitated salt was filtered, DMF was distilled off under reduced pressure, and a residue thus obtained was subjected to liquid-liquid partition with ethyl acetate and water to obtain an ethyl acetate layer. The ethyl acetate layer thus obtained was concentrated, and thus 155.0 g of a compound (yellow transparent liquid) represented by the following Formula (7) was obtained. 155.0 g of the compound thus obtained was dissolved in a mixed liquid of 500 ml of methanol and 500 ml of methylene chloride, and while the solution was maintained at 20° C. or lower, 199.9 g of hydrazine monohydrate was added dropwise thereto. The mixture was stirred for 12 hours, and then white crystals thus produced were filtered. Thus, 140 g of a compound represented by the following Formula (8) was obtained. The results of NMR, mass analysis, and CHN element analysis are presented below.

$^1$H-NMR (270 MHz, d6-DMSO): δ ppm=9.25 (br, 2H), 7.34 (d, $^3$J=8.4 Hz, 4H), 7.23 (d, $^3$J=8.4 Hz, 4H), 4.29 (br, 4H), 3.60 (s, 4H)

$^{13}$C-NMR (270 MHz, d6-DMSO): δ ppm=167.03, 135.93, 131.91, 131.20, 128.70, 34.41

FD-MS: m/z: 388.3 [M]+

HR-MS (FD): m/z calcd for $C_{22}H_{36}N_4O_2$ [M]+, 394.0592. found 394.0616 elemental analysis: calcd (%) for $C_{16}H_{18}N_4O_2S_3$, C, 48.71; H, 4.60; N, 14.20. found C, 48.93; H, 4.53; N, 14.21.

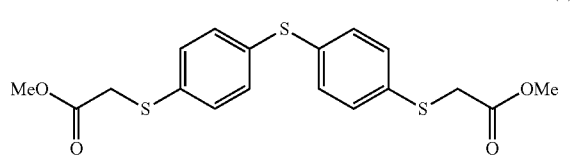

(7)

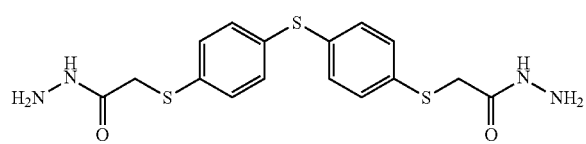

(8)

Synthesis Example 2

10.0 g of 4,4'-thiodiphenol, 21.0 g of methyl bromoacetate, 38.0 g of potassium carbonate, and 50 ml of DMF were mixed, and thus a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate layer thus obtained was concentrated, and 10.0 g of a compound (white solid) represented by the following Formula (9) was obtained. 4 g of the compound thus obtained was dissolved in a mixed liquid of 50 ml of methanol and 50 ml of methylene chloride, and while the solution was maintained at 20° C. or lower, 5.3 g of hydrazine monohydrate was added dropwise thereto. The mixture was stirred for 12 hours, and then white crystals thus produced were filtered. Thus, 3.2 g of a compound represented by the following Formula (10) was obtained. The results of $^1$H-NMR are presented below.

$^1$H-NMR (270 MHz, d6-DMSO): δ ppm=9.32 (br, 2H), 7.24 (d, $^3$J=8.6 Hz, 4H), 6.92 (d, $^3$J=8.6 Hz, 4H), 4.42 (s, 4H), 4.29 (br, 4H).

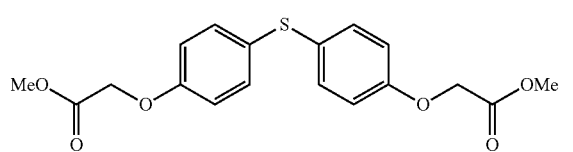

(9)

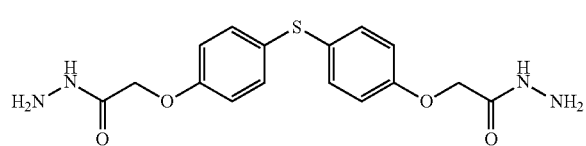

(10)

Synthesis Example 3

10.0 g of 4,4'-methylenediphenol, 22.9 g of methyl bromoacetate, 41.5 g of potassium carbonate, and 50 ml of DMF were mixed, and thus a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate layer thus obtained was concentrated, and 9.2 g of a compound (white solid) represented by the following Formula (11) was obtained. 5 g of the compound thus obtained was dissolved in a mixed liquid of 50 ml of methanol and 50 ml of methylene chloride, and while the solution was maintained at 20° C. or lower, 7.3 g of hydrazine monohydrate was added dropwise thereto. The mixture was stirred for 12 hours, and then white crystals thus produced were filtered. Thus, 4.7 g of a compound represented by the following Formula (12) was obtained. The results for NMR are presented below.

$^1$H-NMR (270 MHz, d6-DMSO): δ ppm=9.27 (br, 2H), 7.11 (d, $^3$J=8.1 Hz, 4H), 6.87 (d, $^3$J=8.4 Hz, 4H), 4.42 (s, 4H), 4.30 (br, 4H), 3.79 (s, 2H).

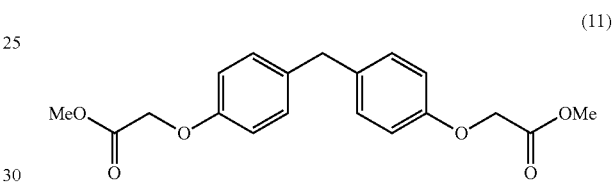

(11)

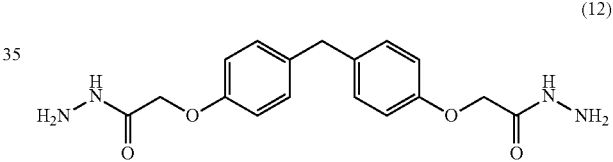

(12)

Synthesis Example 4

10.0 g of 4,4'-sulfonyldiphenol, 18.3 g of methyl bromoacetate, 33.1 g of potassium carbonate, and 50 ml of DMF were mixed, and thus a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate layer thus obtained was concentrated, and thus 8.4 g of a compound (brown solid) represented by the following Formula (13) was obtained. 5 g of the compound thus obtained was dissolved in a mixed liquid of 50 ml of methanol and 50 ml of methylene chloride and while the solution was maintained at 20° C. or lower, 6.3 g of hydrazine monohydrate was added dropwise thereto. The mixture was stirred for 12 hours, and then, white crystals thus produced were filtered. Thus, 3.7 g of a compound represented by the following Formula (14) was obtained. The results of $^1$H-NMR are presented below.

$^1$H-NMR (270 MHz, d6-DMSO): δ ppm=9.22 (br, 2H), 8.06 (d, $^3$J=8.2 Hz, 4H), 7.10 (d, $^3$J=8.4 Hz, 4H), 4.42 (s, 4H), 4.30 (br, 4H).

(13)

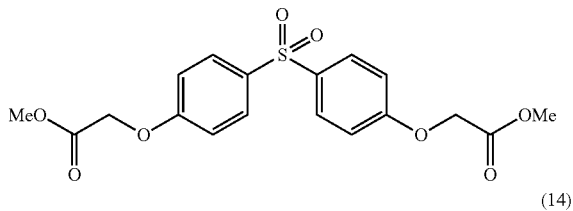

(14)

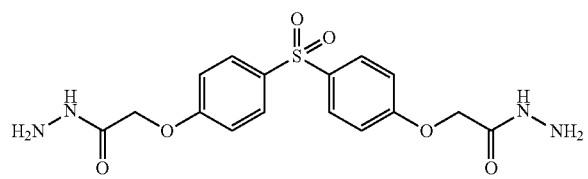

Synthesis Example 5

10.0 g of 4,4'-oxydiphenol, 22.7 g of methyl bromoacetate, 41.0 g of potassium carbonate, and 50 ml of DMF were mixed, and thus a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate layer thus obtained was concentrated, and thus 7.4 g of a compound (brown solid) represented by the following Formula (15) was obtained. 5 g of the compound thus obtained was dissolved in a mixed liquid of 50 ml of methanol and 50 ml of methylene chloride, and while the solution was maintained at 20° C. or lower, 7.2 g of hydrazine monohydrate was added dropwise thereto. The mixture was stirred for 12 hours, and then white crystals thus produced were filtered. Thus, 4.5 g of a compound represented by the following Formula (16) was obtained. The results of NMR are presented below.

$^1$H-NMR (270 MHz, d6-DMSO): δ ppm=9.26 (br, 2H), 7.31 (d, $^3$J=8.6 Hz, 4H), 6.94 (d, $^3$J=8.4 Hz, 4H), 4.48 (s, 4H), 4.25 (br, 4H).

(15)

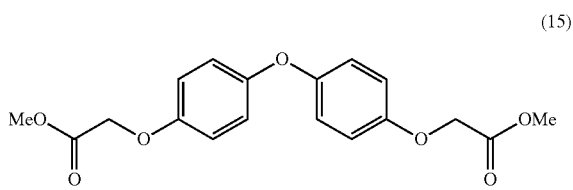

(16)

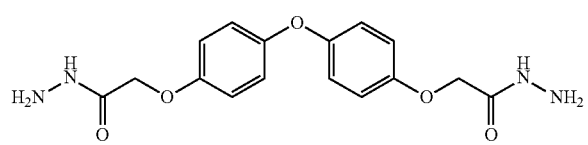

Synthesis Example 6

10.0 g of 4,4'-isopropylidenediphenol, 20.1 g of methyl bromoacetate, 36.3 g of potassium carbonate, and 50 ml of DMF were mixed, and thus a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate thus obtained was concentrated, and thus 12.3 g of a compound (transparent liquid) represented by the following Formula (17) was obtained. 6 g of the compound thus obtained was dissolved in a mixed liquid of 50 ml of methanol and 50 ml of methylene chloride, and while the solution was maintained at 20° C. or lower, 8.1 g of hydrazine monohydrate was added dropwise thereto. The mixture was stirred for 12 hours, and then white crystals thus produced were filtered. Thus, 7.9 g of a compound represented by the following Formula (18) was obtained. The results of NMR are presented below.

$^1$H-NMR (270 MHz, d6-DMSO): δ ppm=9.34 (br, 2H), 7.16 (d, $^3$J=8.6 Hz, 4H), 6.88 (d, $^3$J=8.4 Hz, 4H), 4.48 (s, 4H), 4.26 (br, 4H), 1.86 (s, 6H).

(17)

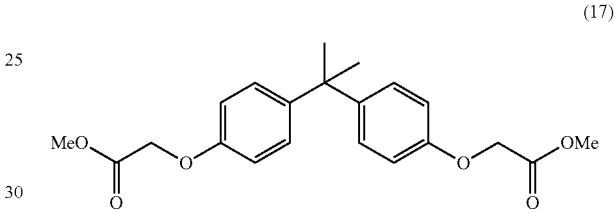

(18)

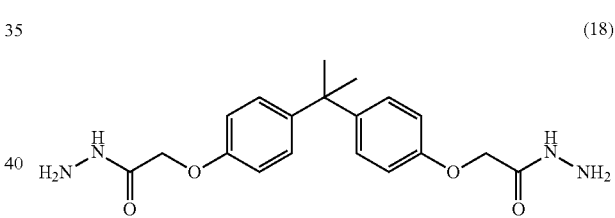

Synthesis Example 7

10.0 g of 9,9-bis(4-hydroxyphenyl)fluorene, 8.8 g of methyl bromoacetate, and 50 ml of dimethylformamide (DMF) were mixed. While the mixture was maintained at 20° C. or lower, 16.0 g of potassium carbonate was added thereto, and a suspension thus obtained was allowed to react for 3 hours at room temperature. After completion of the reaction, a precipitated salt was filtered, DMF was distilled off under reduced pressure, and the residue thus obtained was subjected to liquid-liquid partition with ethyl acetate or water to obtain an ethyl acetate layer. The ethyl acetate layer thus obtained was concentrated, and 13.8 g of a compound (white solid) represented by the following Formula (29) was obtained. 10.0 g of the compound thus obtained was dissolved in a mixed liquid of 50 ml of methanol and 50 ml of methylene chloride, and while the solution was maintained at 20° C. or lower, 5.06 g of hydrazine monohydrate was added dropwise thereto. The mixture was stirred for 12 hours, and then white crystals thus produced were filtered. Thus, 9.2 g of a compound represented by the following Formula (30) was obtained.

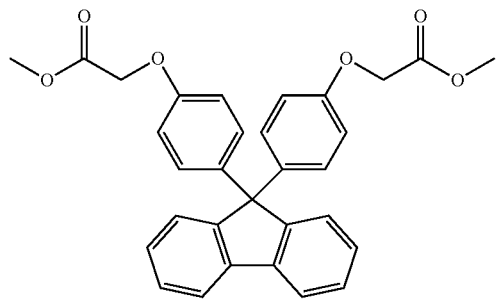

(29)

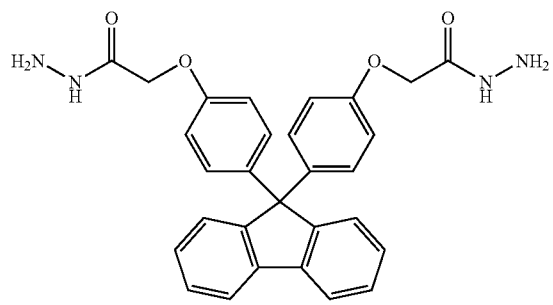

(30)

Synthesis Example 8

10.0 g of 2,3-dihydroxynaphthalene, 19.3 g of methyl bromoacetate, 34.9 g of potassium carbonate, and 50 ml of DMF were mixed, and thus a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate layer thus obtained was concentrated, and 18.7 g of a compound (white solid) represented by the following Formula (31) was obtained. 10 g of the compound thus obtained was dissolved in a mixed liquid of 50 ml of methanol and 50 ml of methylene chloride, and while the solution was maintained at 20° C. or lower, 8.2 g of hydrazine monohydrate was added dropwise thereto. The mixture was stirred for 12 hours, and then white crystals thus produced were filtered. Thus, 8.9 g of a compound represented by the following Formula (32) was obtained.

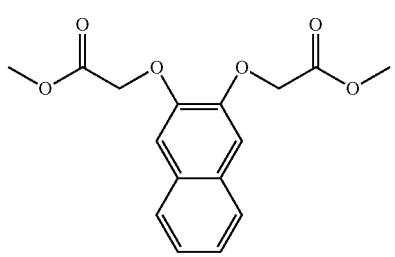

(31)

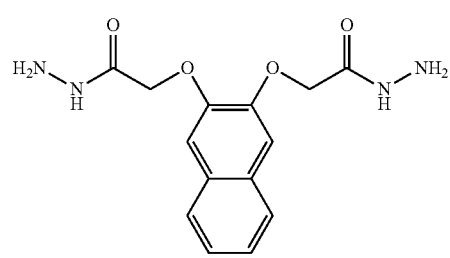

(32)

Synthesis Example 9

10.0 g of 1,1'-bi-2-naphthol, 10.8 g of methyl bromoacetate, 19.5 g of potassium carbonate, and 50 ml of DMF were mixed, and a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate layer thus obtained was concentrated, and thus 14.8 g of a compound (white solid) represented by the following Formula (33) was obtained. 10 g of the compound thus obtained was dissolved in a mixed liquid of 50 ml of methanol and 50 ml of methylene chloride, and while the solution was maintained at 20° C. or lower, 5.8 g of hydrazine monohydrate was added dropwise thereto. The mixture was stirred for 12 hours, and then white crystals thus produced were filtered. Thus, 9.0 g of a compound represented by the following Formula (34) was obtained.

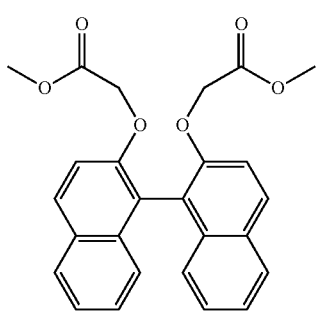

(33)

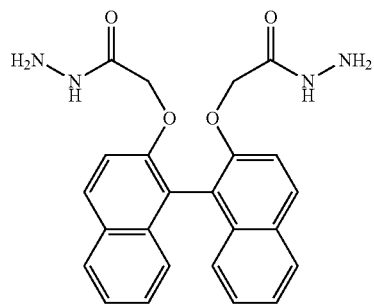

(34)

Synthesis Example 10

10.0 g of 6,6'-dihydroxy-3,3,3',3'-tetramethyl-1,1'-spirobiindane, 10.0 g of methyl bromoacetate, 18.1 g of potassium carbonate, and 50 ml of DMF were mixed, and thus a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate layer thus obtained was concentrated, and thus 14.4 g of a compound (white solid) represented by the following Formula (35) was obtained. 10 g of the compound thus obtained was dissolved in a mixed liquid of 50 ml of methanol and 50 ml of methylene chloride, and while the solution was maintained at 20° C. or lower, 5.5 g of hydrazine monohydrate was added dropwise thereto. The mixture was stirred for 12 hours, and then white crystals thus produced were filtered. Thus, 9.2 g of a compound represented by the following Formula (36) was obtained.

(35)

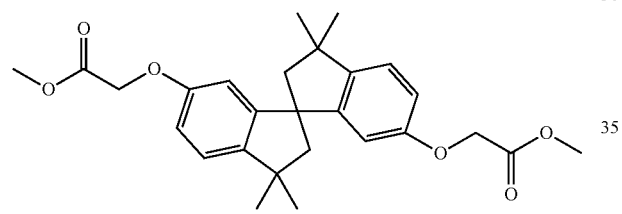

(36)

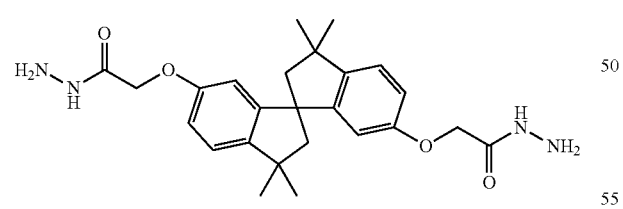

Synthesis Example 11

10.0 g of 4,4'-(α-methylbenzylidene)bisphenol, 10.6 g of methyl bromoacetate, 19.3 g of potassium carbonate, and 50 ml of DMF were mixed, and thus a suspension was obtained. The suspension thus obtained was allowed to react for 24 hours at 80° C. After completion of the reaction, a precipitated salt was filtered, DMF was distilled off under reduced pressure, and the residue thus obtained was subjected to liquid-liquid partition with ethyl acetate and water to obtain an ethyl acetate layer. The ethyl acetate layer thus obtained was concentrated, and thus 14.7 g of a compound (white solid) represented by the following Formula (37) was obtained. 10 g of the compound thus obtained was dissolved in a mixed liquid of 50 ml of methanol and 50 ml of methylene chloride, and while the solution was maintained at 20° C. or lower, 5.8 g of hydrazine monohydrate was added dropwise thereto. The mixture was stirred for 12 hours, and then white crystals thus produced were filtered. Thus, 8.8 g of a compound represented by the following Formula (38) was obtained.

(37)

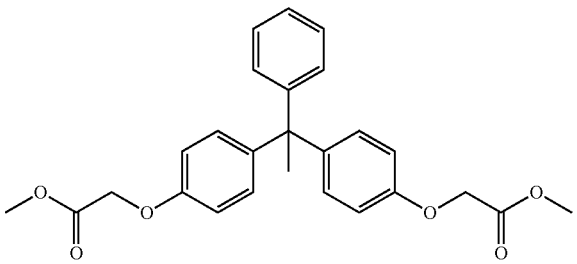

(38)

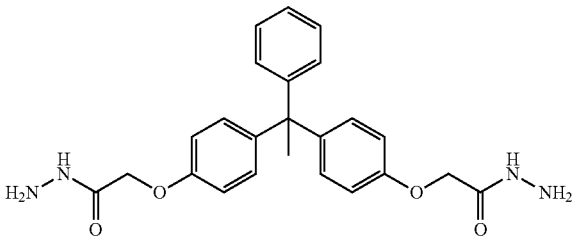

Synthesis Example 12

5.0 g of t-butylhydroquinone (Sigma-Aldrich Co. LLC), 13.8 g of methyl bromoacetate (Sigma-Aldrich Co. LLC), 20.9 g of potassium carbonate, and 100 ml of acetone were mixed, and this suspension was heated to reflux for 12 hours. After cooling, a salt was filtered, and acetone was distilled off under reduced pressure. The residue thus obtained was subjected to liquid-liquid partition with ethyl acetate and water, and an ethyl acetate layer was obtained. The ethyl acetate layer thus obtained was concentrated, and thus 9.0 g of a compound (white solid) represented by the following Formula (44) was obtained.

5.0 g of this compound was dissolved in 30 ml of methanol, and 4.0 g of hydrazine monohydrate was added thereto. After dropwise addition, the mixture was stirred for 12 hours, and 40 ml of water was added thereto. The mixture was stored in a refrigerator (4° C.) for 3 days. A solid thus produced was filtered, and thus 3.2 g of a compound represented by the following Formula (45) was obtained.

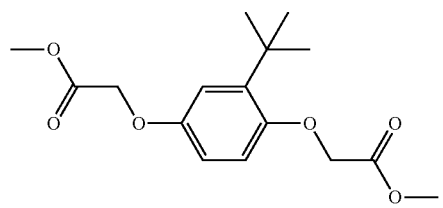

(44)

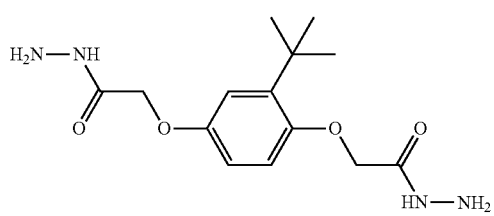

(45)

Synthesis Example 13

5.0 g of 3-hydroxybenzaldehyde (Sigma-Aldrich Co. LLC), 5.0 g of bis[2-(2-chloroethoxy)ethyl]ether (Fluka Corp.), 15.0 of potassium carbonate, and 0.1 g of potassium iodide were suspended in 50 ml of dimethylformamide, and the suspension was allowed to react for 30 hours at 90° C. After cooling, a salt was filtered, and dimethylformamide was distilled off under reduced pressure. The residue thus obtained was subjected to liquid-liquid partition with ethyl acetate and water, and was washed with a 5 mass % aqueous solution of potassium hydrogen carbonate, and thus an ethyl acetate layer was obtained. The ethyl acetate layer thus obtained was concentrated, and thus a brown transparent oil was obtained. This liquid was purified by column chromatography (silica was used for the fixed phase, and a mixed liquid of dichloromethane and ethyl acetate at a volume ratio of 3:1 was used for the mobile phase), and thus 5.1 g of a colorless transparent oily compound represented by the following Formula (46) was obtained.

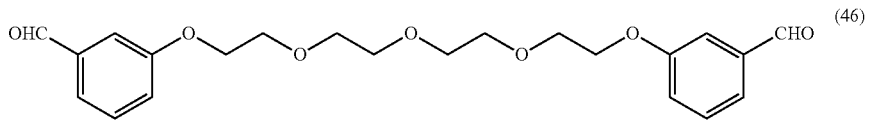 [SMILES: O=Cc1cccc(OCCOCCOCCOCCOc2cccc(C=O)c2)c1]

(46)

Example 1

1.5 g of the compound represented by Formula (8) obtained in Synthesis Example 1, and 510.0 mg of isophthalaldehyde were dissolved in 10 ml of DMF. Trifluoroacetic acid was added thereto at a proportion of 0.05 mol % (proportion to C=N), and the mixture was allowed to react for 3 hours at 60° C. The solution was transferred into a Petri dish made of Teflon (registered trademark), and the solution was retained there at 110° C. under a nitrogen gas stream until most of the solvent evaporated. Thereafter, the solution was dried under reduced pressure at 180° C. for 12 hours. As a result, a colorless transparent film formed from a polymer compound (resin) containing a repeating unit represented by the following Formula (19) was obtained. The results of measuring various property values of the film thus obtained are presented in Table 1. Furthermore, the results for NMR are described below. The acylhydrazone bond equivalent of the compound thus obtained was 246.32.

$^1$H-NMR (270 MHz, d6-DMSO): δ ppm=11.60 (br, 2H), 8.21, 8.00 (br, 2H), 7.88 (t, $^3$J=8.0 Hz, 1H), 7.69 (br, 1H), 7.45 (br, 1H), 7.35 (br, 4H), 7.18 (br, 4H), 4.13, 3.79 (br, 4H).

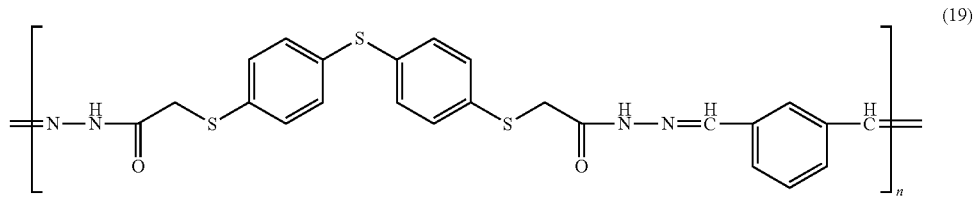

(19)

Example 2

A colorless transparent film formed from a polymer compound (resin) containing a repeating unit represented by the following Formula (20) was obtained in the same manner as in Example 1 described above, except that the compound represented by Formula (10) obtained in Synthesis Example 2 was used instead of the compound represented by Formula (8). The results of measuring various property values of the film thus obtained are presented in Table 1. Furthermore, the results for NMR are described below. The acylhydrazone bond equivalent of the compound thus obtained was 230.25.

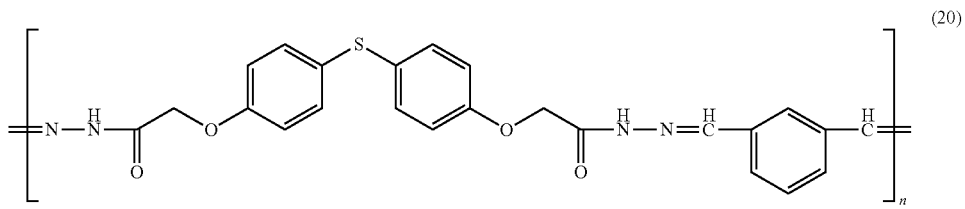

(20)

¹H-NMR (270 MHz, d6-DMSO): δ ppm=11.59 (br, 2H), 8.24, 8.05 (br, 2H), 7.80 (br, 1H), 7.69 (br, 2H), 7.45 (br, 1H), 7.12 (br, 4H), 6.82 (br, 4H), 4.95, 4.61 (br, 4H).

Example 3

A colorless transparent film formed from a polymer compound (resin) containing a repeating unit represented by the following Formula (21) was obtained in the same manner as in Example 1 described above, except that the compound represented by Formula (12) obtained in Synthesis Example 3 was used instead of the compound represented by Formula (8). The results of measuring various property values of the film thus obtained are presented in Table 1. Furthermore, the results for NMR are described below. The acylhydrazone bond equivalent of the compound thus obtained was 221.24.

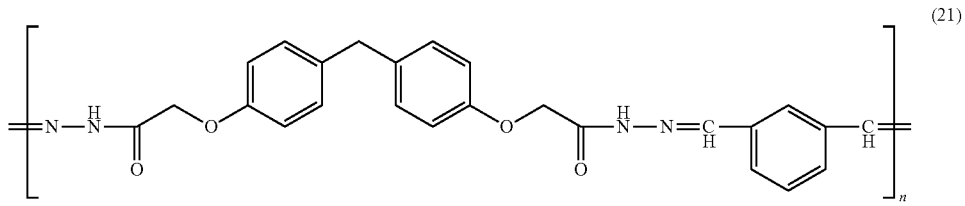

(21)

¹H-NMR (270 MHz, d6-DMSO): δ ppm=11.55 (br, 2H), 8.19, 7.99 (br, 2H), 7.84 (br, 1H), 7.69 (br, 2H), 7.42 (br, 1H), 7.12 (br, 4H), 7.13 (br, 4H), 4.98, 4.61 (br, 4H), 3.85 (br, 2H).

Example 4

A colorless transparent film formed from a polymer compound (resin) containing a repeating unit represented by the following Formula (22) was obtained in the same manner as in Example 1 described above, except that the compound represented by Formula (18) obtained in Synthesis Example 6 was used instead of the compound represented by Formula (8). The results of measuring various property values of the film thus obtained are presented in Table 1. Furthermore, the results for NMR are described below. The acylhydrazone bond equivalent of the compound thus obtained was 235.26.

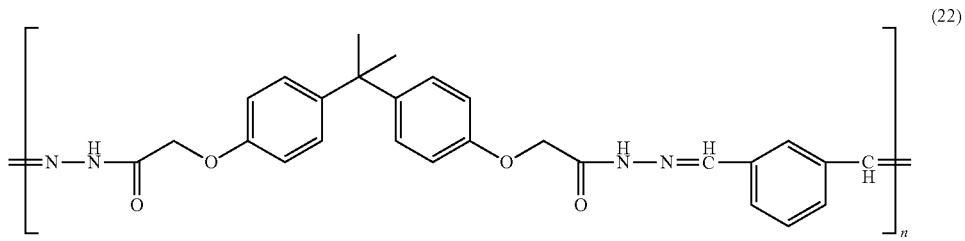

(22)

$^1$H-NMR (270 MHz, d6-DMSO): δ ppm=11.60 (br, 2H), 8.32, 8.01 (br, 2H), 7.70 (br, 2H), 7.46 (br, 1H), 7.08 (br, 4H), 6.89 (br, 2H), 6.79 (br, 2H), 5.07, 4.60 (br, 4H), 1.53 (s, 6H).

Comparative Examples 1 and 2

As a Comparative Example, a PC polycarbonate (manufactured by Sigma-Aldrich Co. LLC, product No.: 25037-45-0) (Comparative Example 1) and a polyether naphthalene (manufactured by DuPont Teijin Films Corp., Teonex) (Comparative Example 2), which are representative thermoplastic resins, were used.

Sheets having a thickness of 50 μm and a width of 10 mm were produced by hot pressing, and the refractive indices and light transmittances of the sheets thus obtained were measured.

As indicated in Table 1, it is obvious that the films obtained in Examples 1 to 4 all have high refractive indices, as compared even with the representative thermoplastic resins of Comparative Examples 1 and 2. Particularly, when both X and Y in Formula (1') are "S (sulfur)" (Example 1), it can be seen that the refractive index is markedly high.

Example 5

A colorless transparent film formed from a polymer compound (resin) containing a repeating unit represented by the following Formula (23) was obtained in the same manner as in Example 1 described above, except that 2,6-pyridinedicarboxyaldehyde was used instead of isophthalaldehyde. The results of measuring the refractive index ($n_D^{25}$) of the film thus obtained are presented in Table 2. Furthermore, the results for NMR are described below. The acylhydrazone bond equivalent of the compound thus obtained was 246.81.

TABLE 1

| | Example 1 | Example 2 | Example 3 | Example 4 |
|---|---|---|---|---|
| Common structure | | | | |
| Structure of part A | | | | |
| $n_D^{25}$ | 1.74 | 1.69 | 1.67 | 1.66 |
| Tg(° C.) | 152 | 185 | 175 | 199 |
| $T_{dec}$1wt(° C.) | 302 | 322 | 324 | 323 |
| $T_{dec}$5wt(° C.) | 324 | 345 | 346 | 349 |
| Density (g/cm³) | 1.55 | 1.48 | 1.46 | 1.43 |
| Number average molecular weight | 72,000 | 74,000 | 55,000 | 65,000 |
| Total light transmittance | 87% | 87% | 88% | 88% |
| Elastic modulus (Gpa) | 2.9 | 3.3 | 3.3 | 3.2 |
| Tensile strength (MPa) | 80 | 86 | 90 | 94 |
| Tensile elongation (%) | 4.7 | 5.2 | 5.4 | 8.2 |

| | Comparative Example 1 | Comparative Example 2 |
|---|---|---|
| Common structure | Polycarbonate | Polyether naphthalene |
| Structure of part A | | |
| $n_D^{25}$ | 1.59 | 1.65 |
| Tg(° C.) | 150 | 113 |
| $T_{dec}$1wt(° C.) | — | — |
| $T_{dec}$5wt(° C.) | — | — |
| Density (g/cm³) | — | — |
| Number average molecular weight | — | — |
| Total light transmittance | 91% | 91% |
| Elastic modulus (Gpa) | — | — |
| Tensile strength (MPa) | 91 | 91 |
| Tensile elongation (%) | — | — |

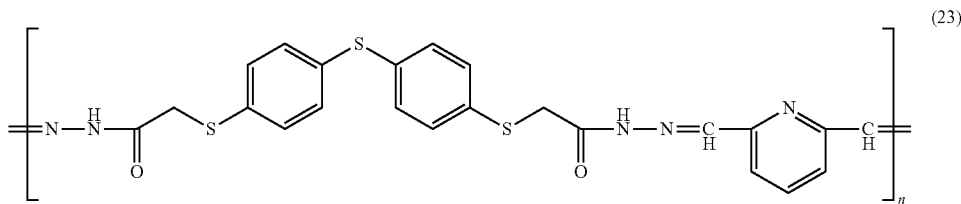

(23)

¹H-NMR (270 MHz, d6-DMSO): δ ppm=11.82 (br, 2H), 8.21, 7.92 (br, 2H), 8.06-7.65 (m, 3H), 7.34 (br, 4H), 7.13 (br, 4H), 4.11, 3.89 (br, 4H).

Example 6

A colorless transparent film formed from a polymer compound (resin) containing a repeating unit represented by the following Formula (24) was obtained in the same manner as in Example 1 described above, except that 2,5-diformylfuran was used instead of isophthalaldehyde. The results of measuring the refractive index ($n_D^{25}$) of the film thus obtained are presented in Table 2. Furthermore, the results for NMR are described below. The acylhydrazone bond equivalent of the compound thus obtained was 241.3.

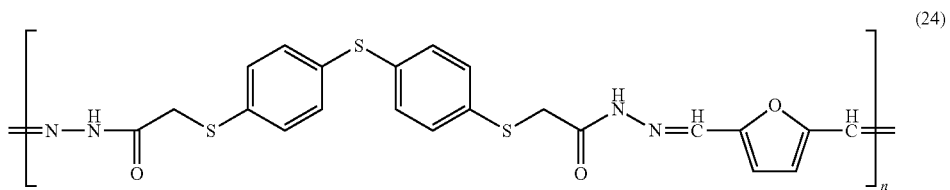

(24)

¹H-NMR (270 MHz, d6-DMSO): δ ppm=11.67 (br, 2H), 8.06, 7.84 (br, 2H), 7.33 (m, 4H), 7.17 (br, 4H), 6.97 (br 2H), 4.06, 3.76 (br, 4H).

Example 7

A colorless transparent film formed from a polymer compound (resin) containing a repeating unit represented by the following Formula (25) was obtained in the same manner as in Example 1 described above, except that 2,5-thiophenedicarboxyaldehyde was used instead of isophthalaldehyde. The results of measuring the refractive index ($n_D^{25}$) of the film thus obtained are presented in Table 2. Furthermore, the results for NMR are described below. The acylhydrazone bond equivalent of the compound thus obtained was 249.33.

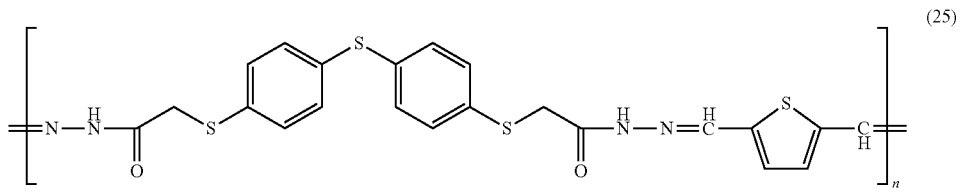

(25)

$^1$H-NMR (270 MHz, d6-DMSO): δ ppm=11.67 (br, 2H), 8.34, 8.08 (br, 2H), 7.43-7.30 (m, 6H), 7.19 (br, 4H), 4.03, 3.75 (br, 4H).

TABLE 2

|  | Example 1 | Example 5 | Example 6 | Example 7 |
|---|---|---|---|---|
| Common structure | | | | |
| Structure of part Z | | | | |
| $n_D^{25}$ | 1.74 | 1.74 | 1.77 | 1.79 |
| Number average molecular weight (Mn) | 72,000 | 38,000 | 32,000 | 26,000 |

Example 8

A colorless transparent film formed from a polymer compound (resin) containing a repeating unit represented by the following Formula (26) was obtained in the same manner as in Example 1 described above, except that (i) the compound represented by Formula (18) obtained in Synthesis Example 6 was used instead of the compound represented by Formula (8), and (ii) 2,6-pyridinedicarboxyaldehyde was used instead of isophthalaldehyde. The results of measuring the refractive index ($n_D^{25}$) of the film thus obtained are presented in Table 3. Furthermore, the results for NMR are described below. The acylhydrazone bond equivalent of the compound thus obtained was 235.76.

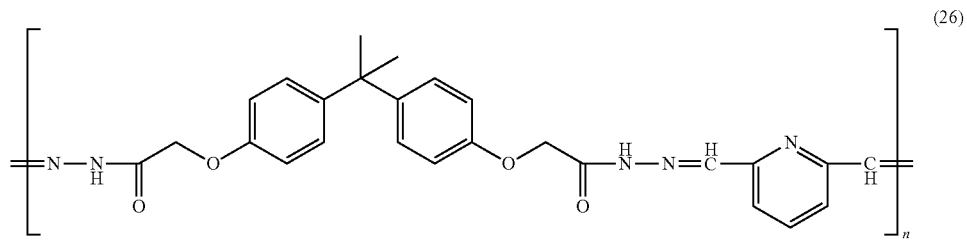

(26)

$^1$H-NMR (270 MHz, d6-DMSO): δ ppm=11.82 (br, 2H), 8.21, 7.92 (br, 2H), 8.06-7.65 (m, 3H), 7.34 (br, 4H), 7.13 (br, 4H), 4.11, 3.89 (br, 4H), 1.53 (s, 6H).

Example 9

A colorless transparent film formed from a polymer compound (resin) containing a repeating unit represented by the following Formula (27) was obtained in the same manner as in Example 1 described above, except that (i) the compound represented by Formula (18) obtained in Synthesis Example 6 was used instead of the compound represented by Formula (8), and (ii) 2,5-diformylfuran was used instead of isophthalaldehyde. The results of measuring various property values of the film thus obtained are presented in Table 3. Furthermore, the results for NMR are described below. The acylhydrazone bond equivalent of the compound thus obtained was 230.24.

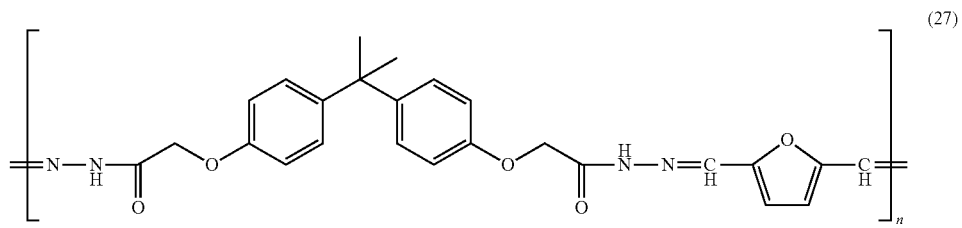

(27)

$^1$H-NMR (270 MHz, d6-DMSO): δ ppm=11.60 (br, 2H), 8.24, 7.92 (br, 2H), 7.10 (br, 4H), 6.96-6.85 (m, 6H), 5.02, 4.60 (br, 4H), 1.54 (s, 6H).

Example 10

A colorless transparent film formed from a polymer compound (resin) containing a repeating unit represented by the following Formula (28) was obtained in the same manner as in Example 1 described above, except that (i) the compound represented by Formula (18) obtained in Synthesis Example 6 was used instead of the compound represented by Formula (8), and (ii) 2,5-thiophenedicarboxyaldehyde was used instead of isophthalaldehyde. The results of measuring various property values of the film thus obtained are presented in Table 3. Furthermore, the results for NMR are described below. The acylhydrazone bond equivalent of the compound thus obtained was 238.28.

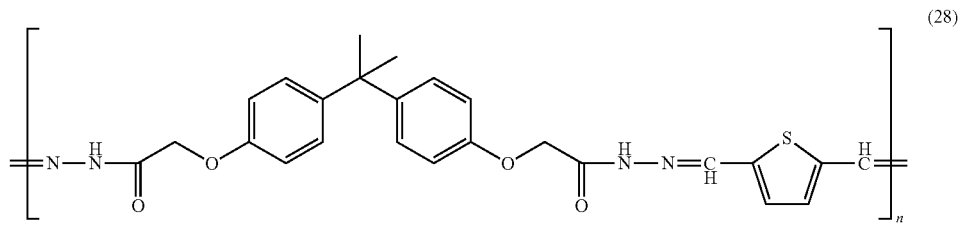

(28)

$^1$H-NMR (270 MHz, d6-DMSO): δ ppm=11.59 (br, 2H), 8.52, 8.12 (br, 2H), 7.38 (s, 2H), 7.10 (br, 4H), 6.87 (br, 4H), 4.99, 4.59 (br, 4H), 1.55 (s, 6H).

TABLE 3

| | Example 4 | Example 8 | Example 9 | Example 10 |
|---|---|---|---|---|
| Common structure | | | | |

TABLE 3-continued

| | Example 4 | Example 8 | Example 9 | Example 10 |
|---|---|---|---|---|
| Structure of part Z | (benzene ring with H substituents) | (pyridine ring with H substituents) | (furan ring with H substituents) | (thiophene ring with H substituents) |
| $n_D^{25}$ | 1.66 | 1.66 | 1.66 | 1.66 |
| Number average molecular weight (Mn) | 65,000 | 54,000 | 32,000 | 34,000 |

As shown in Tables 2 and 3, it is obvious that the films obtained in Examples 5 to 10 all have high refractive indices. Meanwhile, it is understood that when X in Formula (1') represents a less bulky group (Examples 1 and 5 to 7), the films have higher refractive indices as compared with the case where X represents a bulky group (Examples 4 and 8 to 10). Furthermore, when X and Y in Formula (1') both represent "S (sulfur)" (Examples 1 and 5 to 7), it is obvious that the refractive index increases when "Z" in Formula (1') is changed.

Example 11

1.5 g of the compound represented by Formula (30) obtained in Synthesis Example 7 and 4006.8 mg of isophthalaldehyde were dissolved in 10 ml of DMF. Trifluoroacetic acid was added thereto at a proportion of 0.05 mol % (proportion to C=N), and the mixture was allowed to react for 3 hours at 60° C. This was retained at 110° C. under a nitrogen gas stream, until most of the solvent evaporated. Thereafter, drying was carried out under reduced pressure at 180° C. for 12 hours. As a result, a colorless transparent film formed from a polymer compound (resin) containing a repeating unit represented by the following Formula (39) was obtained. The results of measuring various property values of the film thus obtained are presented in Table 4. The acylhydrazone bond equivalent of the compound thus obtained was 296.32.

was added thereto at a proportion of 0.05 mol % (proportion to C=N), and the mixture was allowed to react for 3 hours at 60° C. This was retained at 110° C. under a nitrogen gas stream, until most of the solvent evaporated. Thereafter, drying was carried out under reduced pressure at 180° C. for 12 hours. As a result, a colorless transparent film formed from a polymer compound (resin) containing a repeating unit represented by the following Formula (40) was obtained. The results of measuring various property values of the film thus obtained are presented in Table 4. The acylhydrazone bond equivalent of the compound thus obtained was 201.2.

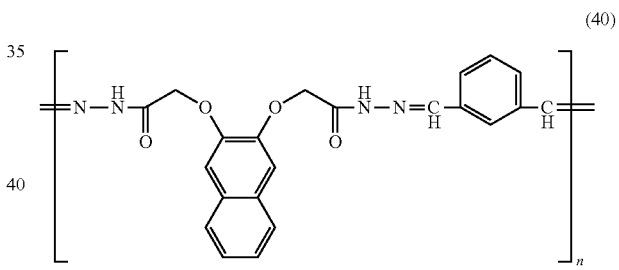

(40)

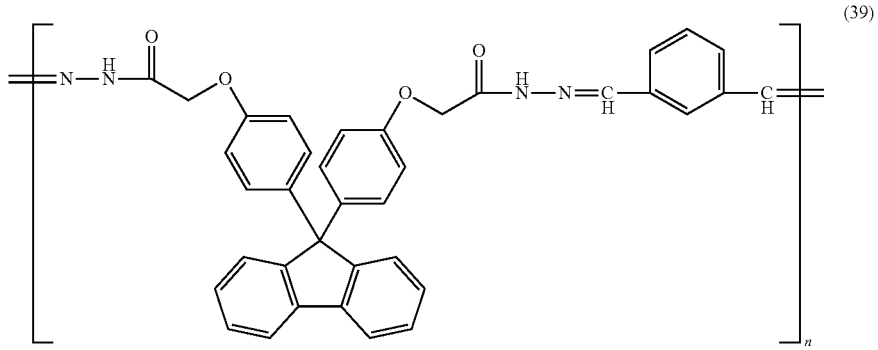

(39)

Example 12

1.5 g of the compound represented by Formula (32) obtained in Synthesis Example 8, and 661.2 mg of isophthalaldehyde were dissolved in 10 ml of DMF. Trifluoroacetic acid Example 13

1.5 g of the compound represented by Formula (34) obtained in Synthesis Example 9, and 467.4 mg of isophthalaldehyde were dissolved in 10 ml of DMF. Trifluoroacetic acid was added thereto at a proportion of 0.05 mol % (proportion to C=N), and the mixture was allowed to react for 3 hours at 60° C. This was retained at 110° C. under a nitrogen gas stream, until most of the solvent evaporated. Thereafter, drying was carried out under reduced pressure at 180° C. for 12 hours. As a result, a colorless transparent film formed from a polymer compound (resin) containing a repeating unit represented by the following Formula (41) was obtained. The results of measuring various property values of the film thus obtained are presented in Table 4. The acylhydrazone bond equivalent of the compound thus obtained was 264.28.

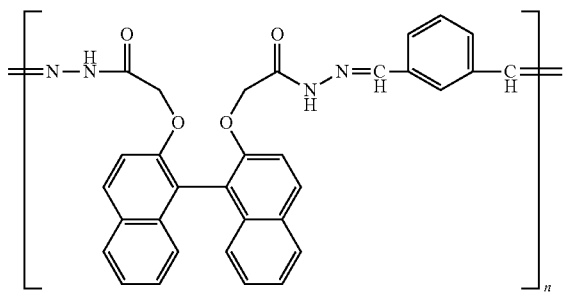

(41)

Example 14

1.5 g of the compound represented by Formula (36) obtained in Synthesis Example 10, and 444.6 mg of isophthalaldehyde were dissolved in 10 ml of DMF. Trifluoroacetic acid was added thereto at a proportion of 0.05 mol % (proportion to C=N), and the mixture was allowed to react for 3 hours at 60° C. This was retained at 110° C. under a nitrogen gas stream, until most of the solvent evaporated. Thereafter, drying was carried out under reduced pressure at 180° C. for 12 hours. As a result, a colorless transparent film formed from a polymer compound (resin) containing a repeating unit represented by the following Formula (42) was obtained. The results of measuring various property values of the film thus obtained are presented in Table 1. The acylhydrazone bond equivalent of the compound thus obtained was 275.33.

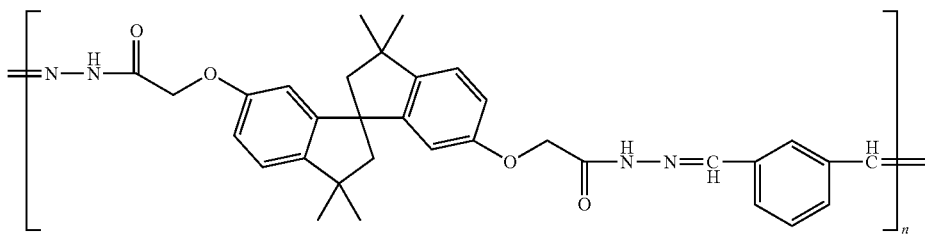

(42)

Example 15

1.5 g of the compound represented by Formula (38) obtained in Synthesis Example 11, and 444.6 mg of isophthalaldehyde were dissolved in 10 ml of DMF. Trifluoroacetic acid was added thereto at a proportion of 0.05 mol % (proportion to C=N), and the mixture was allowed to react for 3 hours at 60° C. This was retained at 110° C. under a nitrogen gas stream, until most of the solvent evaporated. Thereafter, drying was carried out under reduced pressure at 180° C. for 12 hours. As a result, a colorless transparent film formed from a polymer compound (resin) containing a repeating unit represented by the following Formula (43) was obtained. The results of measuring various property values of the film thus obtained are presented in Table 4. The acylhydrazone bond equivalent of the compound thus obtained was 266.3.

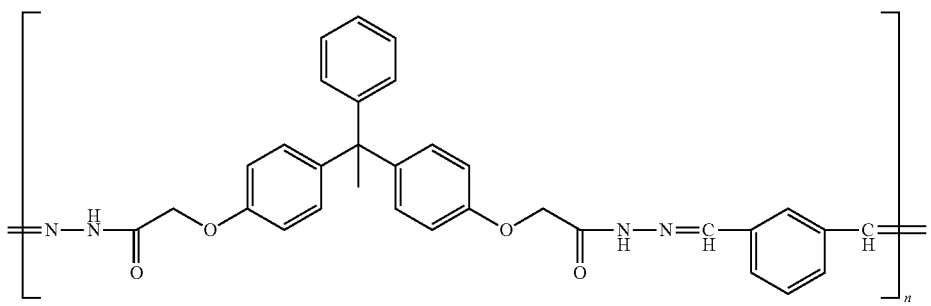

(43)

Comparative Example 3

Polyphenylsulfone (manufactured by Sigma-Aldrich Co. LLC, product No.: 428310), which is a representative thermoplastic resin, was used. A sheet having a thickness of 50 μm and a width of 10 mm was produced by hot pressing, and the refractive index and light transmittance of the sheet thus obtained were measured.

110° C. under a nitrogen gas stream, until most of the solvent evaporated. Thereafter, drying was carried out for 12 hours at 180° C., and thus a colorless transparent film formed from a polymer compound (resin) having a repeating unit represented by Formula (19) was obtained. The number average molecular weight of the resin thus obtained was 64,000. The acylhydrazone bond equivalent of the resin thus obtained was

TABLE 4

|  | Example 11 | Example 12 | Example 13 | Example 14 | Example 15 |
|---|---|---|---|---|---|
| Common structure | \multicolumn{5}{c}{ structure with N—N—C—A—C—N—N=C-phenyl-C } |
| Structure of part A | (fluorene bis-methoxyphenyl) | (dimethoxynaphthalene) | (binaphthyl dimethoxy) | (spirobiindane dimethoxy) | (triphenylmethane bis-methoxyphenyl) |
| $n_D^{25}$ | 1.68 | 1.70 | 1.71 | 1.62 | 1.66 |
| Total light transmittance (%) | 89 | 88 | 88 | 90 | 89 |
| Number average molecular weight | 70,000 | 63,000 | 71,000 | 68,000 | 58,000 |
| Tg (° C.) | 225 | 199 | 204 | 221 | 215 |

|  | Comparative Example 1 | Comparative Example 2 | Comparative Example 3 |
|---|---|---|---|
| Common structure | Polycarbonate | Polyether naphthalene | Polyphenylsulfone |
| Structure of part A |  |  |  |
| $n_D^{25}$ | 1.59 | 1.65 | 1.67 |
| Total light transmittance (%) | 91 | 91 | 89 |
| Number average molecular weight | — | — | — |
| Tg (° C.) | — | — | — |

As shown in Table 4, resins that contained an acylhydrazone bond in the repeating unit and had a number average molecular weight of 500 to 500,000 and an acylhydrazone bond equivalent of 100 to 4,000 (Examples 11 to 15) all had high refractive indices. Furthermore, the total light transmittances thereof were also equivalent to those of conventional films (Comparative Examples 1 to 3).

Example 16

1.5 g of the compound represented by Formula (8) obtained in Synthesis Example 1, and 507.0 mg of isophthalaldehyde were dissolved in 10 ml of DMF. Trifluoroacetic acid was added thereto at a proportion of 0.05 mol % (proportion to C=N), and the mixture was allowed to react for 3 hours at 60° C. The solution obtained after reaction was applied on a glass plate using an applicator, and the glass plate was retained at 246.32. The result of measuring the transmittance of the film thus obtained is presented in Table 5.

Example 17

A colorless transparent film formed from a polymer compound (resin) containing a repeating unit represented by the above Formula (19) was obtained in the same manner as in Example 16 described above, except that 1.81 mg of benzaldehyde (amount of addition (molar amount) of the end-capping agent relative to the molar amount of the terminal groups contained in the resin: 40%) was used in addition to the compound represented by Formula (8) obtained in Synthesis Example 1 and isophthalaldehyde. The number average molecular weight of the resin thus obtained was 64,000. The acylhydrazone bond equivalent of the resin thus obtained was 246.32. The result of measuring the transmittance of the film thus obtained is presented in Table 5. The molar amount of the terminal groups in the resin thus produced was calculated from the number average molecular weight of the resin. Meanwhile, in this Example, since the mole number of the dihydrazide compound was larger than the mole number of the dialdehyde compound as a raw material, the ends of the resin were mostly acylhydrazine ends.

Example 18

A colorless transparent film formed from a polymer compound (resin) containing a repeating unit represented by the above Formula (19) was obtained in the same manner as in Example 16 described above, except that 3.63 mg of benzaldehyde (amount of addition (molar amount) of the end-capping agent relative to the molar amount of the terminal groups contained in the resin: 80%) was used in addition to the compound represented by Formula (8) obtained in Synthesis Example 1 and isophthalaldehyde. The number average molecular weight of the resin thus obtained was 64,000. The acylhydrazone bond equivalent of the resin thus obtained was 246.32. The result of measuring the transmittance of the film thus obtained is presented in Table 5.

Example 19

A colorless transparent film formed from a polymer compound (resin) containing a repeating unit represented by Formula (19) was obtained in the same manner as in Example 16 described above, except that 4.54 mg of benzaldehyde (amount of addition (molar amount) of the end-capping agent relative to the molar amount of the terminal groups contained in the resin: 100%) was used in addition to the compound represented by Formula (8) obtained in Synthesis Example 1 and isophthalaldehyde. The number average molecular weight of the resin thus obtained was 64,000. The acylhydrazone bond equivalent of the resin thus obtained was 246.32. The result of measuring the transmittance of the film thus obtained is presented in Table 5.

Example 20

A colorless transparent film formed from a polymer compound (resin) containing a repeating unit represented by Formula (19) was obtained in the same manner as in Example 16 described above, except that 5.44 mg of benzaldehyde (amount of addition (molar amount) of the end-capping agent relative to the molar amount of the terminal groups contained in the resin: 120%) was used in addition to the compound represented by Formula (8) obtained in Synthesis Example 1 and isophthalaldehyde. The number average molecular weight of the resin thus obtained was 61,000. The acylhydrazone bond equivalent of the resin thus obtained was 246.32. The result of measuring the transmittance of the film thus obtained is presented in Table 5.

Example 21

A colorless transparent film formed from a polymer compound (resin) containing a repeating unit represented by Formula (19) was obtained in the same manner as in Example 16 described above, except that 6.35 mg of benzaldehyde (amount of addition (molar amount) of the end-capping agent relative to the molar amount of the terminal groups contained in the resin: 140%) was used in addition to the compound represented by Formula (8) obtained in Synthesis Example 1 and isophthalaldehyde. The number average molecular weight of the resin thus obtained was 58,000. The acylhydrazone bond equivalent of the resin thus obtained was 246.32. The result of measuring the transmittance of the film thus obtained is presented in Table 5.

Example 22

A colorless transparent film formed from a polymer compound (resin) containing a repeating unit represented by Formula (19) was obtained in the same manner as in Example 16 described above, except that 6.01 mg of 4-chlorobenzaldehyde (amount of addition (molar amount) of the end-capping agent relative to the molar amount of the terminal groups contained in the resin: 100%) was used in addition to the compound represented by Formula (8) obtained in Synthesis Example 1 and isophthalaldehyde. The number average molecular weight of the resin thus obtained was 64,000. The acylhydrazone bond equivalent of the resin thus obtained was 246.32. The result of measuring the transmittance of the film thus obtained is presented in Table 5.

Example 23

A colorless transparent film formed from a polymer compound (resin) containing a repeating unit represented by Formula (19) was obtained in the same manner as in Example 16 described above, except that 4.36 mg of acetic anhydride (amount of addition (molar amount) of the end-capping agent relative to the molar amount of the terminal groups contained in the resin: 100%) was used in addition to the compound represented by Formula (8) obtained in Synthesis Example 1 and isophthalaldehyde. The number average molecular weight of the resin thus obtained was 64,000. The acylhydrazone bond equivalent of the resin thus obtained was 246.32. The result of measuring the transmittance of the film thus obtained is presented in Table 5.

Example 24

A colorless transparent film formed from a polymer compound (resin) containing a repeating unit represented by Formula (19) was obtained in the same manner as in Example 16 described above, except that 4.28 mg of succinic anhydride (amount of addition (molar amount) of the end-capping agent relative to the molar amount of the terminal groups contained in the resin: 100%) was used in addition to the compound represented by Formula (8) obtained in Synthesis Example 1 and isophthalaldehyde. The number average molecular weight of the resin thus obtained was 64,000. The acylhydrazone bond equivalent of the resin thus obtained was 246.32. The result of measuring the transmittance of the film thus obtained is presented in Table 5.

TABLE 5

| | End-capping agent | Amount of addition of end-capping agent (%) | 400 nm |
|---|---|---|---|
| Example 16 | — | — | 42.0 |
| Example 17 | Benzaldehyde | 40 | 52.2 |
| Example 18 | Benzaldehyde | 80 | 62.4 |
| Example 19 | Benzaldehyde | 100 | 72.2 |
| Example 20 | Benzaldehyde | 120 | 64.3 |
| Example 21 | Benzaldehyde | 140 | 50.9 |
| Example 22 | 4-Chlorobenzaldehyde | 100 | 49.9 |
| Example 23 | Acetic anhydride | 100 | 62.7 |
| Example 24 | Succinic anhydride | 100 | 64.6 |

Figure 4:
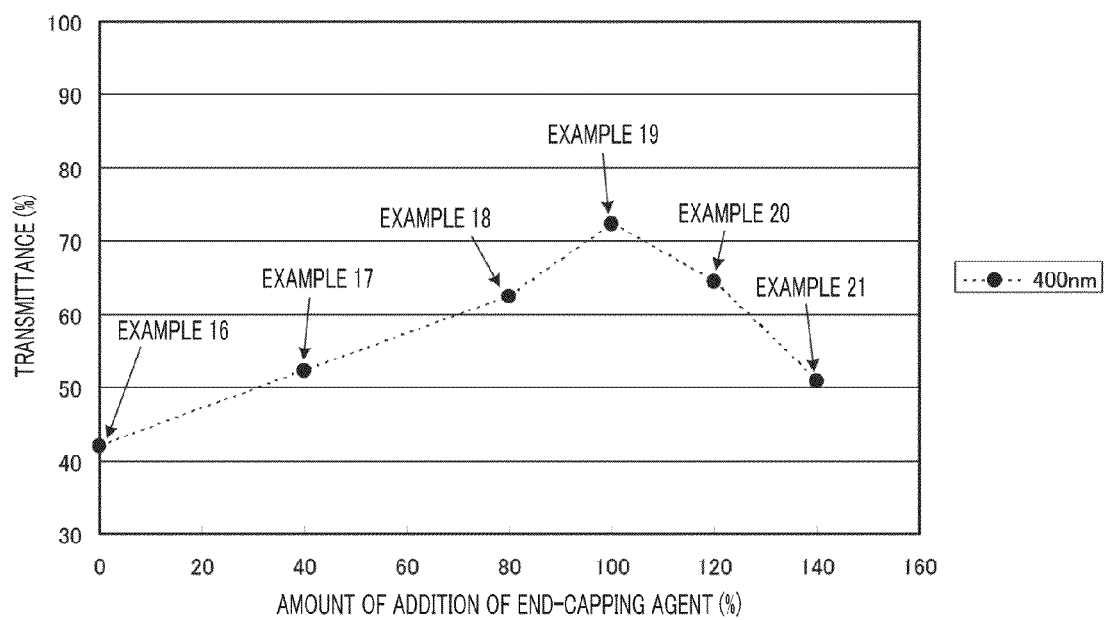
FIG. 4 is a graph showing the relationship between the amount of addition (%) of an end-capping agent and the transmittance (%) to light having a wavelength of 400 nm in the films produced in Examples 16 to 21.

When the acylhydrazine end of the resin was capped with an end-capping agent (Examples 17 to 24), the transmittance to light having a wavelength of 400 nm became satisfactory as compared with the case where the acylhydrazine end was not capped (Example 16). FIG. 4 illustrates the relationship between the transmittance to light having a wavelength 400 nm and the amount of addition of benzaldehyde (end-capping agent) in Examples 16 to 21. As shown in FIG. 4, when the amount of addition of benzaldehyde (end-capping agent) increased, the transmittance to light having a wavelength of 400 nm increased. Particularly, when the molar amount of addition of the end-capping agent relative to the total molar amount of ends of the resin was set to 100%, the light transmittance was very high. However, the end-capping agent was further added in excess, the transmittance decreased. This is speculated to be because when an end-capping agent was added in excess, aldehyde ends were exposed, and the resin lost transparency.

Furthermore, as shown in Table 5, when a comparison was made for the case where the end-capping agent was benzaldehyde (Example 19), the case where the end-capping agent was 4-chloroaldehyde (Example 22), the case where the end-capping agent was acetic anhydride (Example 23), and the case where the end-capping agent was succinic anhydride (Example 24), the transmittance to light having a wavelength of 400 nm was high in the case where the end-capping agent was benzaldehyde. It is speculated to be because when benzaldehyde is used as an end-capping agent, there are fewer reactive functional groups at the ends.

Example 25

A colorless transparent film formed from a polymer compound (resin) containing a repeating unit represented by the following Formula (47) was obtained in the same manner as in Example 1 described above, except that the compound represented by Formula (8) was changed to the compound represented by Formula (45) obtained in Synthesis Example 12, and isophthalaldehyde was changed to the compound represented by Formula (46) obtained in Synthesis Example 13.

factured by Meisyo Kiko Co., Ltd., NM-0501). Specifically, the film was heated to 185° C., and a mold (lattice pattern; difference in height of concavo-convexity: 10 μm, convex part shape: quadrangular pyramid, width of convex part (length of a lower side of the quadrangular pyramid): 10 μm, width of concave part (interval between quadrangular pyramids): 10 μm) was pressed at a press pressure of 5 MPa for 60 seconds.

Figure 1B:
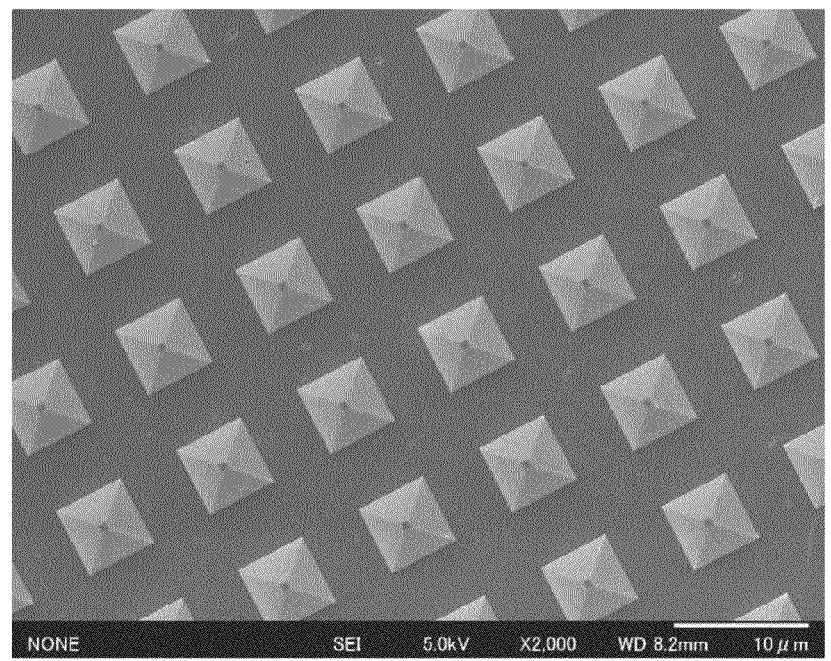
FIG. 1B is a partial magnified image of FIG. 1A.

According to the method described above, a film having a fine structure formed on the surface was observed by scanning electron microscopy (SEM). The observed images are presented in FIG. 1A and FIG. 1B. FIG. 1B is a partial magnified image of FIG. 1A. As shown in FIG. 1A and FIG. 1B, a high-precision pattern was reproduced on the film.

Example 27

A fine structure was formed on a film in the same manner as in Example 26, except that the mold used in Example 26 was changed to a mold (honeycomb-shaped pattern; difference in height of concavo-convexity: 10 μm, convex part shape: hexagonal cylinder shape, length of one side of the hexagon: 50 μm, width of concave part (interval between hexagonal cylinders): 10 μm).

Figure 2A:
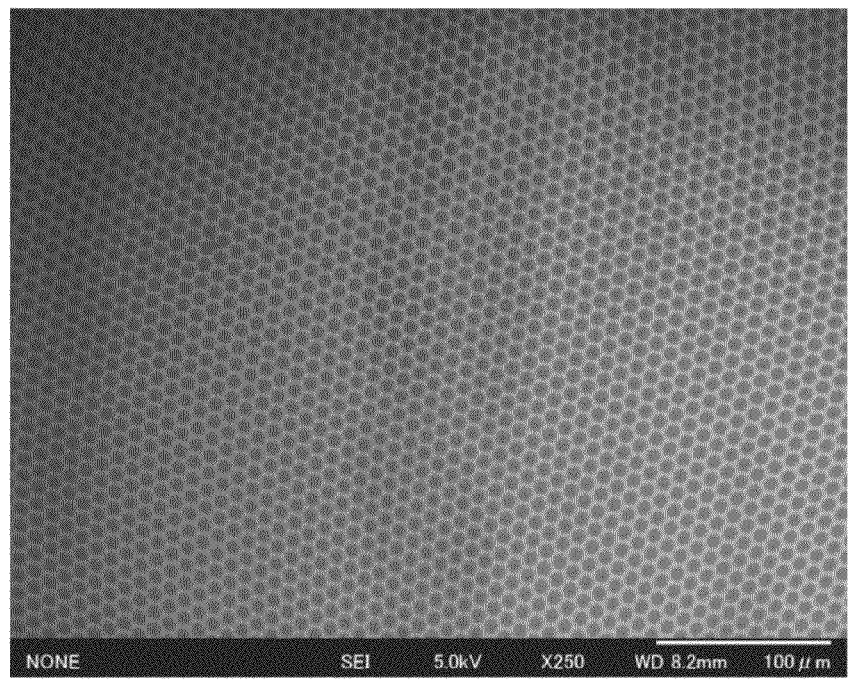
FIG. 2A is an image obtained by observing a fine structure produced in a film in Example 27, with a scanning electron microscope (SEM)
Figure 2B:
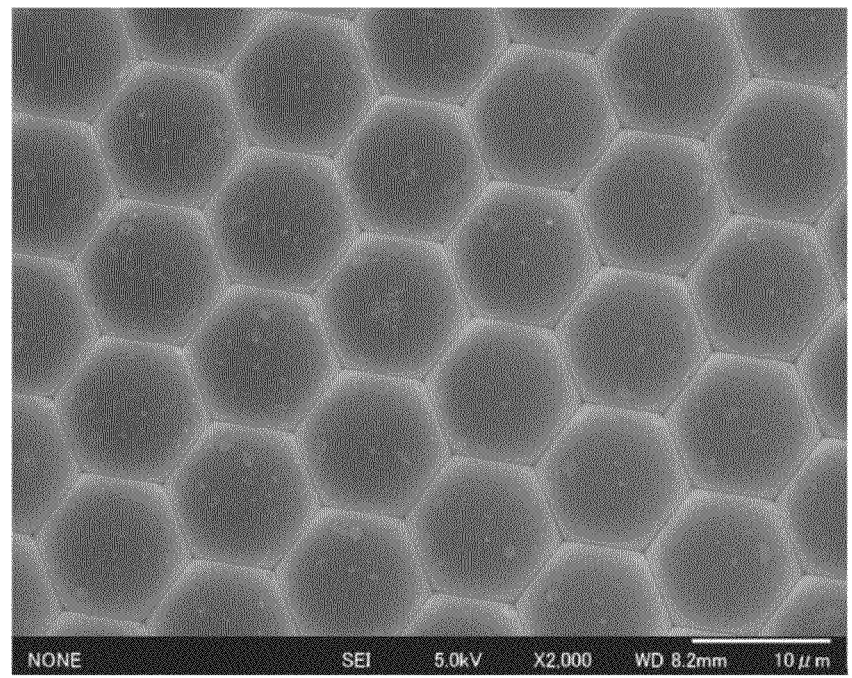
FIG. 2B is a partial magnified image of FIG. 2A.

A film having a fine structure formed on the surface was observed with scanning electron microscopy (SEM). The observed images are presented in FIG. 2A and FIG. 2B. FIG. 2B is a partial magnified image of FIG. 2A. As shown in FIG. 2A and FIG. 2B, a high-precision pattern was reproduced on the film.

Example 28

A sputtered thin film formed from indium tin oxide (ITO) was laminated on the film produced in Example 1. Lamination of the ITO thin film was carried out using a sputtered thin film forming apparatus (manufactured by Ulvac, Inc.; JSP-8000). The film thickness of the ITO film obtained after film formation was 50 nm to 100 nm.

For the film prior to the ITO film lamination (film produced in Example 1) and the film obtained after the ITO film lami-

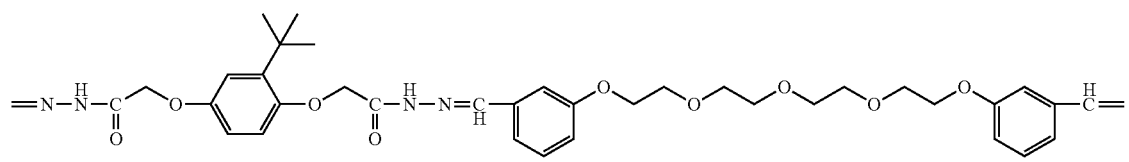

(47)

A colorless transparent film formed from a polymer compound (resin) containing a repeating unit represented by Formula (47) was obtained. The number average molecular weight of the resin thus obtained was 68,000. Furthermore, the acylhydrazone bond equivalent was 338.38. The refractive index $n_D^{25}$ of this film was 1.59, and the glass transition temperature (Tg) was 63° C. The resin described above had a lower glass transition temperature and a lower refractive index $n_D^{25}$ as compared with the resins of Examples 1 to 15. This is speculated to be because the molecular chain of the group Z of Formula (1') was long, and the density of the resin was low.

Example 26

Figure 3:
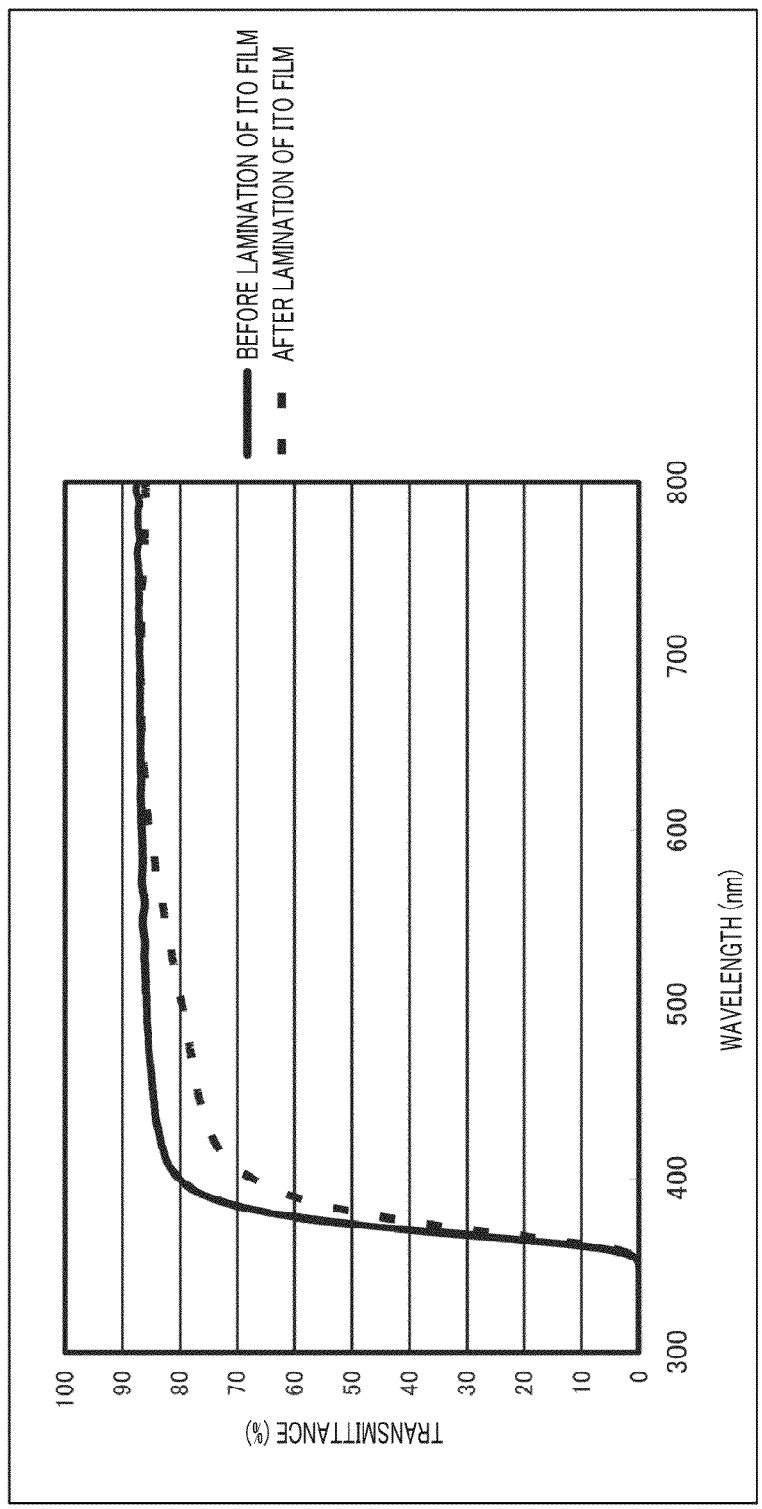
FIG. 3 is a graph showing the total light transmittance of a film containing the resin of the present application produced in Example 1 (prior to the lamination of an ITO film), and the total light transmittance of the relevant film after having an ITO film laminated thereon in Example 28.

A film (film thickness: 20 μm to 100 μm) produced in Example 1 was imprint molded using a nanoimprinter (manunation, measurement of the total light transmittance was carried out by the method described above. The results of measuring the total light transmittance are presented in the graph of FIG. 3.

In general, when the adhesiveness between a film and an ITO film is low, the state of lamination of the ITO film is deteriorated, and the total light transmittance after the ITO film lamination is greatly deteriorated. On the contrary, according to the graph of FIG. 3, the total light transmittance of the film obtained after the ITO film lamination was slightly decreased as compared with the film prior to the ITO film lamination, but the total light transmittance did not change greatly. Therefore, a film formed from the resin of the present application has satisfactory adhesiveness to an ITO film.

Example 29

1.5 g of the compound represented by Formula (8) obtained in Synthesis Example 1, and 510.0 mg of isophthalaldehyde were dissolved in 10 ml of DMF. Trifluoroacetic acid was added thereto at a proportion of 0.05 mol % (proportion to C=N), and the mixture was allowed to react for 3 hours at 60° C. The reaction solution was applied on a glass plate, a SUS plate, and a polyimide film (Capton H type; manufactured by DuPont Toray Co., Ltd.), and the substrates were retained at 110° C. under a nitrogen gas stream until most of the solvent evaporated. Thereafter, the substrates were dried for 12 hours at 180° C. As a result, colorless transparent films formed from a polymer compound (resin) containing a repeating unit represented by Formula (19) were obtained.

[Evaluation]

The various laminates produced in Example 29 were respectively immersed in water for 24 hours, and the adhesiveness between the films and the various substrates was checked. The evaluation results are shown below. The evaluation of adhesiveness was carried out such that the case where the film was detached was rated as X; and the case where the film was not detached even after immersion for 24 hours was rated as ○. The results are presented in the following Table 6.

TABLE 6

|  | Glass plate | SUS plate | Polyimide film |
|---|---|---|---|
| Evaluation of adhesiveness | x | ○ | ○ |

From the above Table 6, it is shown that films from the resin of the present application have excellent adhesiveness to a SUS plate and a polyimide film.

Example 30

1.5 g of the compound represented by Formula (8) obtained in Synthesis Example 1, and 510.0 mg of isophthalaldehyde was dissolved in 10 ml of DMF. Trifluoroacetic acid was added thereto at a proportion of 0.05 mol % (proportion to C=N), and the mixture was allowed to react for 3 hours at 60° C. A mold releasing agent (Zelec UN (registered trademark); manufactured by DuPont Company) was added to the reaction solution in an amount of 0.0002 g, and the solution was applied on a glass plate, a SUS plate and a polyimide film (Capton H type; manufactured by DuPont Toray Co., Ltd.). The substrates were retained at 110° C. under a nitrogen gas stream until most of the solvent evaporated, and subsequently, the substrates were dried at 180° C. for 3 hours. As a result, films containing a mold releasing agent and a polymer compound (resin) containing a repeating unit represented by Formula (19) were obtained. The amount of addition of the mold releasing agent was 0.01 parts by weight relative to 100 parts by mass of the resin.

Example 31

Films were obtained in the same manner as in Example 30, except that the amount of the mold releasing agent was changed to 0.0006 g. The amount of addition of the mold releasing agent was 0.03 parts by weight relative to 100 parts by mass of the resin.

Example 32

Films were obtained in the same manner as in Example 30, except that the amount of the mold releasing agent was changed to 0.0019 g. The amount of addition of the mold releasing agent was 0.1 parts by weight relative to 100 parts by mass of the resin.

Example 33

Films were obtained in the same manner as in Example 30, except that the amount of the mold releasing agent was changed to 0.019 g. The amount of addition of the mold releasing agent was 0.5 parts by weight relative to 100 parts by mass of the resin.

For the laminates obtained after thermal compression, the adhesiveness between the films and the various substrates was checked. In regard to peelability, the case where the film was detached before being immersed in water was rated as ○; the case where the film was detached after being immersed in water for 24 hours was rated as Δ; and the case where the film was not detached even after being immersed in water for 24 hours was rated as x. Furthermore, transparency of the films produced in Examples 29 to 33 was also checked. Transparency was checked by visual inspection, and the case where transparency was high was rated as ○; and the case where white turbidness occurred was rated as x. These evaluation results are presented in Table 7.

TABLE 7

|  | Example 29 | Example 30 | Example 31 | Example 32 | Example 33 |
|---|---|---|---|---|---|
| Amount of incorporation of mold releasing agent relative to 100 parts by mass of resin (parts by mass) | 0 | 0.01 | 0.03 | 0.1 | 0.5 |
| Peelability from glass plate | Δ | Δ | ○ | ○ | ○ |
| Peelability from SUS plate | x | Δ | ○ | ○ | ○ |
| Peelability from polyimide film | x | Δ | ○ | ○ | ○ |
| Transparency of film | ○ | ○ | ○ | ○ | x |

According to the results of Table 7, in Example 29 where a mold releasing agent was not incorporated, the peelability between the films and the various substrates was low. When a mold releasing agent was incorporated in an amount of 0.01 parts by mass or more relative to 100 parts by mass of the resin, an enhancement of peelability was observed, and when the mold releasing agent was added in an amount of 0.03 parts by mass or more relative to 100 parts by mass of the resin, films could be detached from various substrates before the films were immersed in water. However, when the mold releasing agent was incorporated in an amount of 0.5 parts by mass relative to 100 parts by mass of the resin, the film became cloudy, and transparency decreased.

Example 34

1.5 g of adipic acid dihydrazide and 1154.9 mg of isophthalaldehyde were introduced into 10 ml of DMF (dimethylformamide). Trifluoroacetic acid was added to this solution at a proportion of 0.05 mol % (proportion to C═N bond). The solution was allowed to react for 3 hours at 60° C., and a white suspension was precipitated out. The solution containing the suspension was transferred into a Petri dish made of Teflon (registered trademark) and having an inner diameter of 100 mm, and the solution was retained at 110° C. under a nitrogen gas stream until most of the solvent evaporated. Thereafter, the residue was dried under reduced pressure at 180° C. for 12 hours, and thus a white solid was obtained. The solid was pressed with a hot pressing machine at 2 MPa at 230° C. for 5 minutes, and thus a colorless transparent film formed from a polymer compound (resin) containing a repeating unit represented by the following Formula (48) was obtained. The number average molecular weight of the resin thus obtained was 62,000. The acylhydrazone bond equivalent of the resin was 136.16. The results of measuring various property values of the film are presented in Table 8.

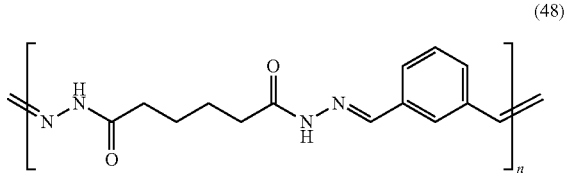

(48)

Example 35

1.5 g of azelaic acid dihydrazide and 930.2 mg of isophthalaldehyde were introduced into 10 ml of DMF. Trifluoroacetic acid was added to this solution at a proportion of 0.05 mol % (proportion to C═N bond). The solution was allowed to react for 3 hours at 60° C., and a white suspension was precipitated out. The solution containing the suspension was transferred into a Petri dish made of Teflon (registered trademark) and having an inner diameter of 100 mm, and the solution was retained at 110° C. under a nitrogen gas stream until most of the solvent evaporated. Thereafter, the residue was dried under reduced pressure at 180° C. for 12 hours, and thus a white solid was obtained. The solid was pressed with a hot pressing machine at 2 MPa at 230° C. for 5 minutes, and thus a colorless transparent film formed from a polymer compound (resin) containing a repeating unit represented by the following Formula (49) was obtained. The number average molecular weight of the resin thus obtained was 66,000. The acylhydrazone bond equivalent of the resin was 157.2. The results of measuring various property values of the film are presented in Table 8.

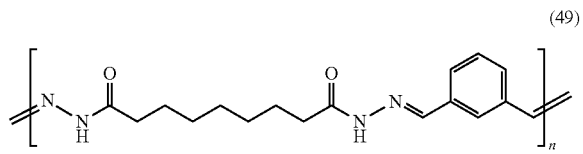

(49)

Example 36

1.5 g of sebacic acid dihydrazide and 873.6 mg of isophthalaldehyde were introduced into 10 ml of DMF. Trifluoroacetic acid was added to this solution at a proportion of 0.05 mol % (proportion to C═N bond). The solution was allowed to react for 3 hours at 60° C., and a white suspension was precipitated out. The solution containing the suspension was transferred into a Petri dish made of Teflon (registered trademark) and having an inner diameter of 100 mm, and the solution was retained at 110° C. under a nitrogen gas stream until most of the solvent evaporated. Thereafter, the residue was dried under reduced pressure at 180° C. for 12 hours, and thus a white solid was obtained. The solid was pressed with a hot pressing machine at 2 MPa at 230° C. for 5 minutes, and thus a colorless transparent film formed from a polymer compound (resin) containing a repeating unit represented by the following Formula (50) was obtained. The number average molecular weight of the resin thus obtained was 59,000. The acylhydrazone bond equivalent of the resin was 164.21. The results of measuring various property values of the film are presented in Table 8.

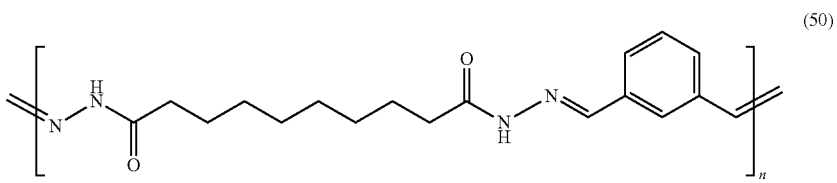

(50)

Example 37

1.5 g of dodecanedioic acid dihydrazide and 778.7 mg of isophthalaldehyde were introduced into 10 ml of DMF. Trifluoroacetic acid was added to this solution at a proportion of 0.05 mol % (proportion to C═N bond). The solution was allowed to react for 3 hours at 60° C., and a white suspension was precipitated out. The solution containing the suspension was transferred into a Petri dish made of Teflon (registered trademark) and having an inner diameter of 100 mm, and the solution was retained at 110° C. under a nitrogen gas stream until most of the solvent evaporated. Thereafter, the residue was dried under reduced pressure at 180° C. for 12 hours, and thus a white solid was obtained. The solid was pressed with a hot pressing machine at 2 MPa at 230° C. for 5 minutes, and thus a colorless transparent film formed from a polymer compound (resin) containing a repeating unit represented by the following Formula (51) was obtained. The number average molecular weight of the resin thus obtained was 63,000. The acylhydrazone bond equivalent of the resin was 178.24. The results of measuring various property values of the film are presented in Table 8.

the polymer chains comprise a repeating unit represented by the following Formula (1):

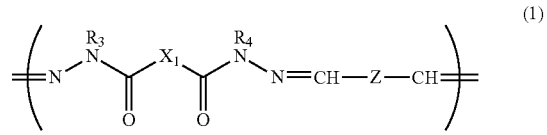

(1)

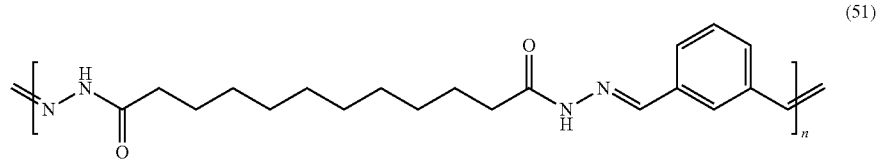

(51)

TABLE 8

| | Example 34 | Example 35 | Example 36 | Example 37 |
|---|---|---|---|---|
| Common structure | ⟨structure⟩ | | | |
| Structure of part A | ⟨alkylene⟩ | ⟨alkylene⟩ | ⟨alkylene⟩ | ⟨alkylene⟩ |
| $n_D^{25}$ | 1.66 | 1.64 | 1.63 | 1.61 |
| Total light transmittance (%) | 89 | 89 | 90 | 90 |
| Number average molecular weight | 62,000 | 66,000 | 59,000 | 63,000 |
| Tg (° C.) | 153 | 134 | 132 | 117 |

As can be seen from Table 8, resins which contained an acylhydrazone bond in the repeating unit, and had a number average molecular weight of 500 to 500,000 and an acylhydrazone bond equivalent of 100 to 4,000, and in which $X_1$ in Formula (1) was an alkylene group (Examples 34 to 37), all had high refractive indices. Furthermore, the total light transmittances thereof were also high.

INDUSTRIAL APPLICABILITY

The resin of the present invention has a high refractive index, high transparency, and excellent heat resistance and molding processability. Therefore, the resin is suitable as an optical material for constructing optical devices such as an optical film, an optical lens, an optical fiber, and a light waveguide.

The invention claimed is:
1. A resin comprising polymer chains having an acylhydrazone bond and aldehyde groups or acylhydrazine groups at their ends, wherein
the resin has a number average molecular weight of 500 to 500,000,
the resin has an acylhydrazone bond equivalent of 100 to 4,000,
at least some polymer chains of the resin are end-capped at their aldehyde end or acylhydrazine end, and wherein in Formula (1),
$X_1$ represents a divalent linking group containing atoms selected from the group consisting of C, H, N, O, S, Si, F, Cl, Br and I and having a molecular weight of 80 to 8,000, in which the number of atoms of the shortest molecular chain that links the carbonyl carbon atoms of two acylhydrazone bonds is 2 to 60;
$R_3$ and $R_4$ each independently represent a hydrogen group, a methyl group, or a phenyl group;
Z represents a group represented by any one of the following Formulas (2) to (6), or a saturated hydrocarbon group having 1 to 12 carbon atoms:

(2)

(3)

-continued

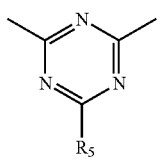
(4)

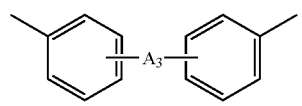
(5)

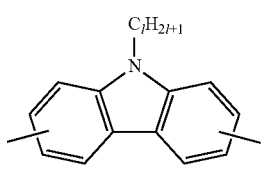
(6)

wherein in Formula (2), $A_1$ represents —CH= or —N=, while the positions of the bonding hands on the aromatic ring are the 2-position and the 6-position, or the 2-position and the 5-position with respect to $A_1$, and the aromatic ring may have a methyl group, an ethyl group or a halogen atom at the other positions;

in Formula (3), $A_2$ represents —CH$_2$—, —O—, —S—, or —N(R)— (wherein R represents a hydrogen atom, a methyl group, or an ethyl group);

in Formula (4), $R_5$ represents a hydrogen atom, a methyl group, an ethyl group, a methoxy group, an ethoxy group, a halogen atom, a methylthio group, or an ethylthio group;

in Formula (5), $A_3$ represents —CH$_2$—, —C(CF$_3$)$_2$—, —S—, —C(CH$_3$)$_2$—, —O—, —SO$_2$—, —S(=O)—, —C(=O)—, —C(=O)NH—, or —O—C$_p$H$_{2p}$—O— (wherein p represents an integer from 2 to 18); and in Formula (6), l represents an integer from 1 to 8.

2. The resin according to claim 1, wherein in Formula (1), $X_1$ represents an alkylene group having 2 to 30 carbon atoms which may be substituted.

3. The resin according to claim 1, wherein $X_1$ in Formula (1) represents any one of the following Formulas (A-1) to (A-3):

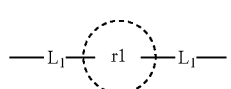
(A-1)

wherein in Formula (A-1), ring r1 represents an aromatic ring which may be substituted;

L1 represents a single bond, or a divalent linking group comprising atoms selected from the group consisting of H, O, C, N and S and having a molecular weight of 500 or less, while two L1's may be identical with or different from each other:

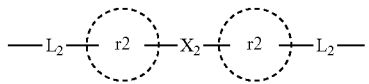
(A-2)

wherein in Formula (A-2), ring r2 represents an aromatic ring which may be substituted, while two ring r2's may be identical with or different from each other;

X2 represents any one of a single bond, —CH2—, —C(CF3)2-, —S—, —C(CH3)2-, —O—, —SO2-, —S(=O)—, —C(=O)NH—, —C(=O)—, a group represented' by the following Formula (1-1), a group represented by the following Formula (1-2), and a group which forms a spiro bond together with two ring r2's; and L2 represents a single bond, or a divalent linking group comprising atoms selected from the group consisting of H, O, C, N and S and having a molecular weight of 500 or less, while two L2's may be identical with or different from each other:

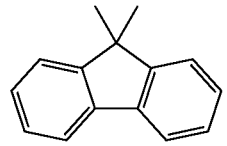
(1-1)

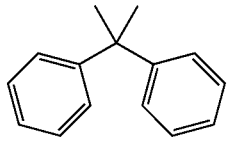
(1-2)

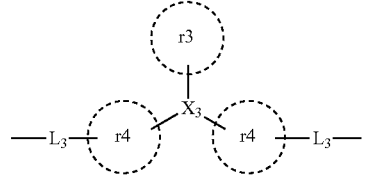
(A-3)

wherein in Formula (A-3), ring r3 and ring r4 each independently represent an aromatic ring which may be substituted, while two ring r4's may be identical with or different from each other;

X3 represents a trivalent or tetravalent carbon atom;

when X3 represents a tetravalent carbon atom, the substituent that is bonded to X3 is any one of a methyl group and a phenyl group; and L3 represents a single bond, or a divalent linking group comprising atoms selected from the group consisting of H, O, C, N and S, and having a molecular weight of 500 or less, while two L3's may be identical with or different from each other.

4. The resin according to claim 3, wherein r1 in Formula (A-1) represents a naphthalene ring.

5. The resin according to claim 3, wherein X2 in Formula (A-2) represents a single bond, and r2 represents a naphthalene ring.

6. The resin according to claim 1, wherein the repeating unit represented by Formula (1) is represented by the following Formula (1'):

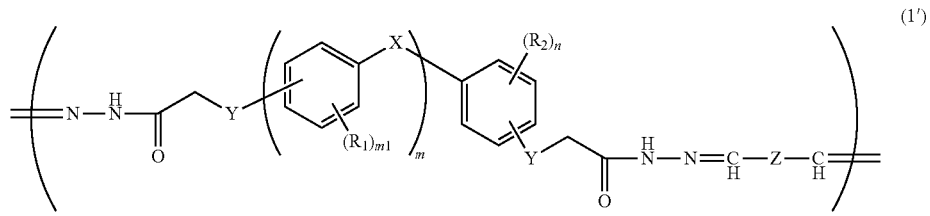

wherein in Formula (1')

X represents any structure selected from —CH2-, —C(CF3)2-, —S—, —C(CH3)2-, —O—, —SO2-, —S(=O)—, —C(=O)NH—, —C(=O)—, a group represented by the following Formula (1-1), and a group represented by the following Formula (1-2);

Y's each independently represent —O—, —CH2- or —S—;

m represents an integer from 0 to 10;

m1 and n each independently represent an integer from 0 to 4;

R1 and R2 each independently represent a methyl group, an ethyl group, a propyl group, a butyl group, a methoxy group, an ethoxy group, an aryl group, an aryloxy group, or a halogen group; and Z represents a group represented by any one of the above Formulas (2) to (6), or a saturated hydrocarbon group having 1 to 12 carbon atoms:

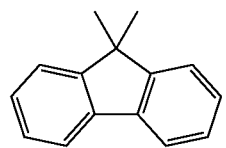 (1-1)

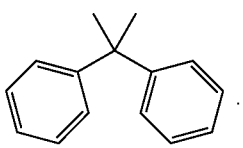 (1-2)

7. The resin according to claim 6, wherein X in the above Formula (1') represent —CH$_2$—, —S—, or —C(CH$_3$)$_2$—.

8. The resin according to claim 6, wherein Z in the above Formula (1') represents a group represented by the above Formula (2) or (3).

9. The resin according to claim 6, wherein X and Y in the above Formula (1') both represent —S—.

10. An optical material comprising:

the resin according to claim 1; and at least one additive selected from the group consisting of inorganic particles, metal particles, and ionic compounds.

11. An optical device comprising the resin according to claim 1.

12. An optical device comprising:

a light emitting element; and a luminous flux control member comprising the resin according to claim 1, which is formed into a shape capable of controlling the luminous flux emitted from the light emitting element.

13. An organic EL device comprising:

an organic EL element;

a transparent electrode layer; and a resin layer comprising the resin according to claim 1.

14. A lens comprising the resin according to claim 1.

* * * * *